US 10,874,423 B2

(12) United States Patent
Tada et al.

(10) Patent No.: US 10,874,423 B2
(45) Date of Patent: Dec. 29, 2020

(54) MEDICAL DEVICE

(71) Applicant: TERUMO KABUSHIKI KAISHA, Tokyo (JP)

(72) Inventors: Yuuichi Tada, Kanagawa (JP); Kousuke Nishio, Kanagawa (JP); Mizuho Hirao, Kanagawa-ken (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 301 days.

(21) Appl. No.: 15/432,978

(22) Filed: Feb. 15, 2017

(65) Prior Publication Data

US 2017/0231657 A1    Aug. 17, 2017

(30) Foreign Application Priority Data

Feb. 15, 2016    (JP) .................................. 2016-026339

(51) Int. Cl.
*A61B 17/3207*    (2006.01)
*A61B 17/32*    (2006.01)
(Continued)

(52) U.S. Cl.
CPC ................ *A61B 17/320758* (2013.01); *A61B 17/320783* (2013.01); *A61B 2017/22039* (2013.01);
(Continued)

(58) Field of Classification Search
CPC ........ A61B 17/320758; A61B 17/3207; A61B 17/320783; A61B 17/320725; A61B 17/32075; A61B 17/32002
See application file for complete search history.

(56) References Cited

U.S. PATENT DOCUMENTS

| 4,950,277 A * | 8/1990 | Farr ................. A61B 17/32075 |
| | | 604/22 |
| 2002/0042622 A1* | 4/2002 | Vargas ................... A61B 17/11 |
| | | 606/153 |

(Continued)

FOREIGN PATENT DOCUMENTS

| CN | 102112175 A | 6/2011 |
| CN | 104853801 A | 8/2015 |

(Continued)

OTHER PUBLICATIONS

Notice of Reasons for Refusal issued by the Japanese Patent Office in corresponding Japanese Patent Application No. 2018-500132 dated Aug. 18, 2020 (6 pages including partial English translation).

(Continued)

*Primary Examiner* — Tuan V Nguyen
(74) *Attorney, Agent, or Firm* — Buchanan Ingersoll & Rooney PC

(57) ABSTRACT

A medical device is disclosed for cutting an object in a living body lumen. The medical device includes a rotatable elongate member, rotating member having a cutting portion cutting the object and disposed on the distal end side of the elongate member for rotating together with rotation of the elongate member; and a distal member having a guide portion disposed on the distal end side of the rotating member with a space left from the rotating member and a supporting portion which supports the guide portion and defines a dimension of the space in an axial direction of the elongate member. The guide portion is disposed at a position at which the guide portion overlaps with part of the cutting portion and exposes part of the cutting portion as viewed from the distal end side of the distal member.

29 Claims, 15 Drawing Sheets

(51) Int. Cl.
*A61B 90/00* (2016.01)
*A61B 17/22* (2006.01)

(52) U.S. Cl.
CPC .............. *A61B 2017/22079* (2013.01); *A61B 2017/320052* (2013.01); *A61B 2017/320064* (2013.01); *A61B 2017/320791* (2013.01); *A61B 2090/08021* (2016.02)

(56) References Cited

U.S. PATENT DOCUMENTS

| 2004/0133223 | A1* | 7/2004 | Weber | A61B 17/32072 606/159 |
| 2007/0010840 | A1* | 1/2007 | Rosenthal | A61B 17/3207 606/170 |
| 2007/0032746 | A1* | 2/2007 | Sell | A61M 25/0127 600/585 |
| 2007/0088230 | A1* | 4/2007 | Terashi | A61M 25/0043 600/585 |
| 2008/0045986 | A1* | 2/2008 | To | A61B 17/32070 606/159 |
| 2010/0087780 | A1* | 4/2010 | Tekulve | A61M 25/09025 604/95.01 |
| 2011/0152791 | A1 | 6/2011 | Kobayashi | |
| 2012/0109171 | A1* | 5/2012 | Zeroni | A61B 17/32075 606/159 |
| 2015/0314108 | A1 | 11/2015 | Kanemasa et al. | |

FOREIGN PATENT DOCUMENTS

| JP | 2014-533147 A | 12/2014 |
| WO | 2015/042190 A2 | 3/2015 |

OTHER PUBLICATIONS

Office Action (The First Office Action) dated Sep. 3, 2020, by the State Intellectual Property Office of People's Republic of China in corresponding Chinese Patent Application No. 201780011370.7 and an English Translation of the Office Action. (13 pages).

* cited by examiner

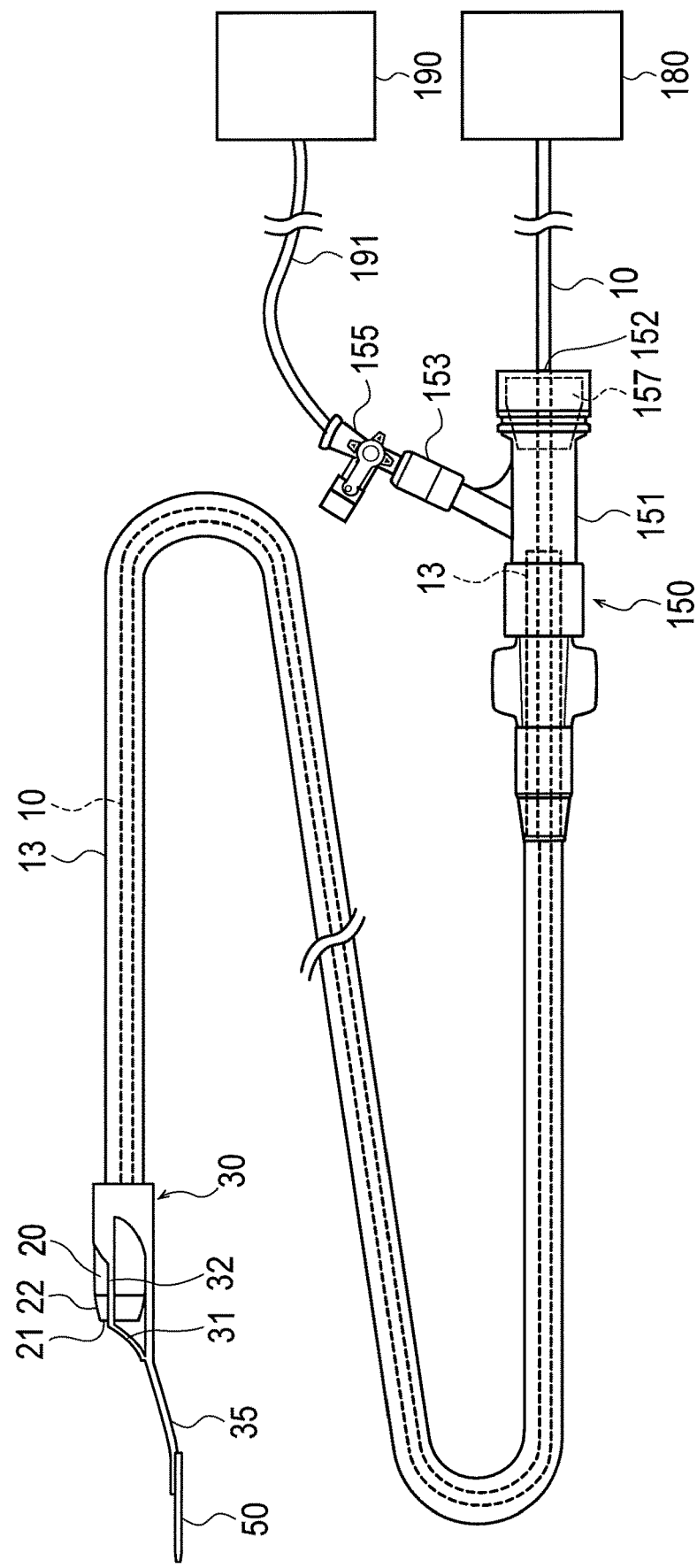

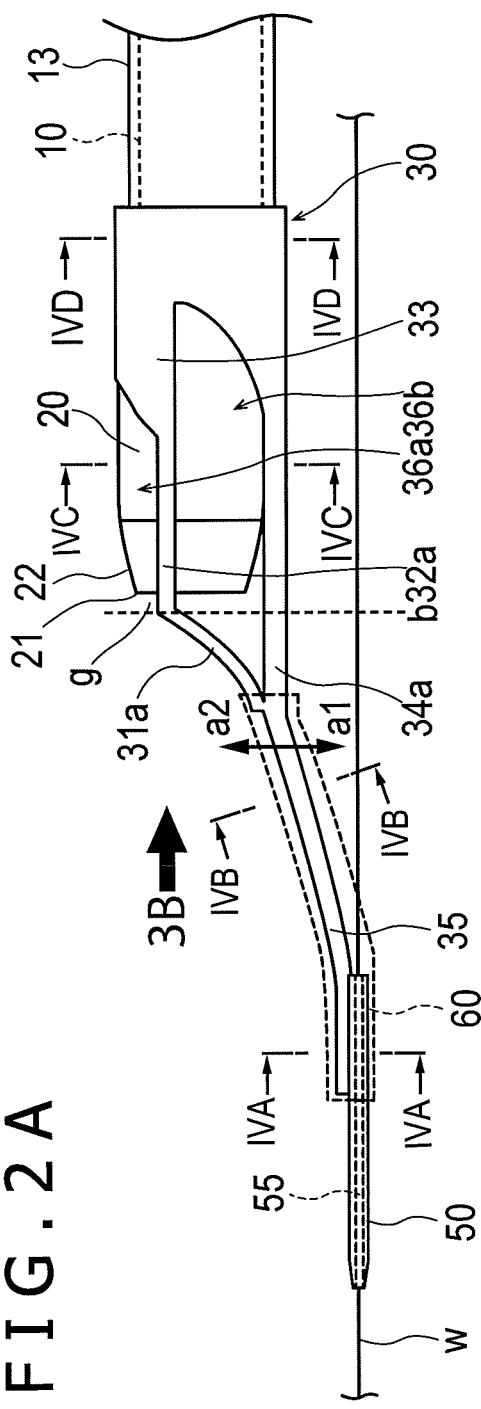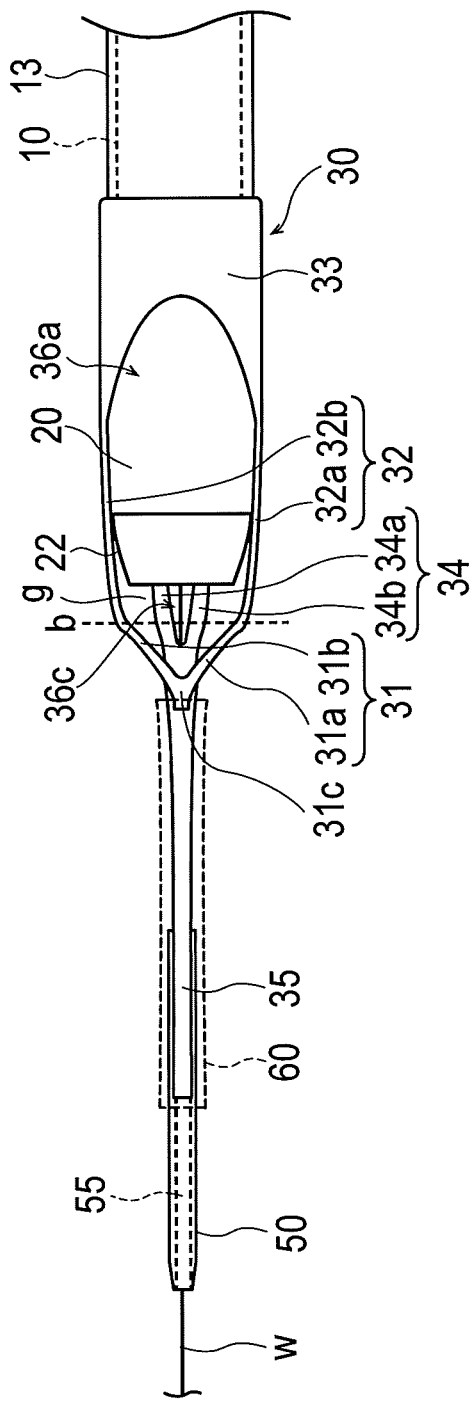

MEDICAL DEVICE

CROSS-REFERENCES TO RELATED APPLICATIONS

This application claims priority to Japanese Patent Application No. 2016-26339 filed on Feb. 15, 2016, the entire content of which is incorporated herein by reference.

TECHNICAL FIELD

The present disclosure relates to a medical device for cutting an object existing in a living body lumen.

BACKGROUND DISCUSSION

As a method of treating a stenosis formed in a blood vessel such as a coronary artery, a treatment using a balloon catheter, a stent indwelling method and so forth are conventionally available. However, it is known that it can be difficult to achieve a therapeutic effect for a long period of time only by expansion of a vascular lumen with a balloon, and indwelling of a stent can cause a new stenosis. Especially, for example, in a complex lesion, such as in a case in which the plaque of the stenosis has become calcified and hardened or in a case in which a stenosis occurs at a branching portion of a blood vessel, and a treatment in which only a balloon catheter or a stent is used may not be able to achieve a sufficient therapeutic effect. Therefore, as a treatment which contributes to extension of a vascular patency period or improvement in treatment results of a complex lesion, atherectomy is noticed by which plaque or calcification lesion which makes a cause of a stenosis or an object such as a thrombus is removed outside the body.

As a medical device for atherectomy, a medical device is proposed, for example, in JP-T-2014-533147. The medical device is structured such that an elongated catheter has, provided at a distal end of the catheter, a rotating member with a cutting portion (blade) which exerts a cutting force on a stenosis.

SUMMARY

In a treatment in which the aforesaid device is used, the rotating cutting portion is contacted with the stenosis to perform a work for scraping off the stenosis. For example, while a treatment is being performed, for example, for a blood vessel having a comparatively small diameter, if such a situation should occur that the cutting portion reaches a blood vessel wall, there is the possibility that the cutting portion may penetrate the blood vessel wall. For such a problem as just described, if the cutting portion is downsized (reduced in diameter) together with the rotating member, the risk that the cutting portion may penetrate the blood vessel wall can be decreased. However, the downsizing of the cutting portion gives rise to decrease of the cutting efficiency.

A medical device is disclosed, which further improves safety when cutting an object of a cutting target.

According to the present disclosure, a medical device is disclosed for cutting an object in a living body lumen includes a rotatable elongate member, a rotating member having a cutting portion cutting the object and disposed on the distal end side of the elongate member for rotating together with rotation of the elongate member, and a distal member having a guide portion disposed on the distal end side of the rotating member with a space left from the rotating member and a supporting portion which supports the guide portion and defines a dimension of the space in an axial direction of the elongate member, the guide portion being disposed at a position at which the guide portion overlaps with part of the cutting portion and exposes part of the cutting portion as viewed from the distal end side of the distal member.

With the medical device according to the present disclosure, when it cuts an object of a cutting target, the guide portion disposed on the distal end side of the rotating member restricts the range within which the cutting portion can cut (range within which the cutting portion and the object contact with each other). Therefore, even if such a situation occurs that the rotating member reaches a wall portion of the living body lumen during a treatment, the guide portion can prevent the rotating member from penetrating the wall portion.

A method is disclosed of cutting an object in a lumen of a living body, the method comprising: introducing a medical device into the lumen of the living body, the medical device including a rotatable elongate member, a rotating member having a cutting portion disposed on a distal end side of the elongate member, a distal member having a guide portion disposed on the distal end side of the rotating member and spaced apart from the rotating member and a supporting portion which supports the guide portion and defines a dimension of a space in an axial direction of the elongate member, and the guide portion being disposed at a position at which the guide portion overlaps with part of the cutting portion and exposes part of the cutting portion as viewed from the distal end side of the distal member; and rotating the rotating member and the elongate member together to cut the object within the lumen of the living body.

The above and other objects, features and advantages of the present disclosure will become apparent from the following description and the appended claims, taken in conjunction with the accompanying drawings in which like parts or elements denoted by like reference characters.

BRIEF DESCRIPTION OF THE DRAWINGS

FIG. 1 is a schematic view depicting a medical device according to an embodiment;

FIG. 2A is a partial lateral view depicting, in an enlarged scale, a distal end portion of the medical device according to the embodiment;

FIG. 26 is a partial plan view depicting, in an enlarged scale, the distal end portion of the medical device according to the embodiment;

DETAILED DESCRIPTION OF THE PREFERRED EMBODIMENT

Figure 3A:
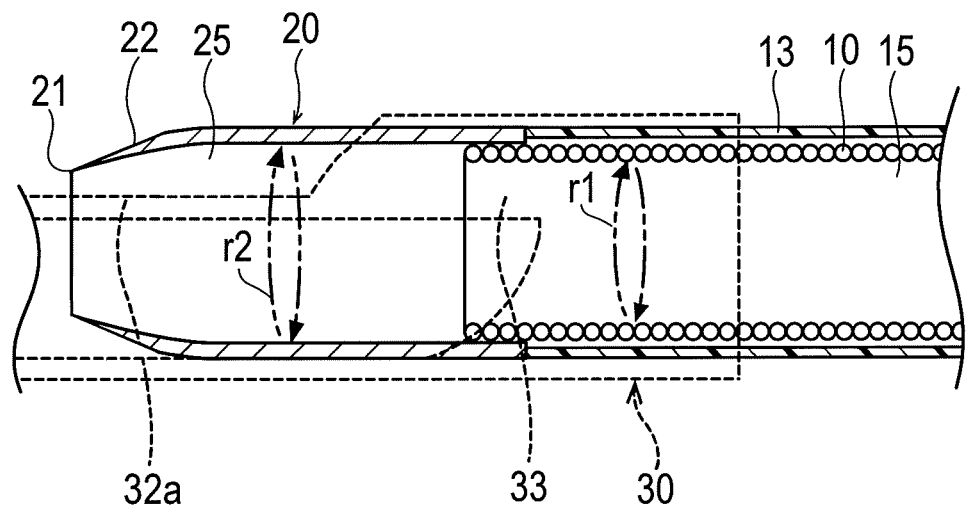
FIG. 3A is a partial sectional view of the medical device taken along an axial direction of a rotating member according to the embodiment.

In the following, an embodiment of the present disclosure is described with reference to the drawings. Note that the dimension ratio in the drawings is exaggerated for the convenience of illustration and is sometimes different from the actual ratio.

Figure 3B:
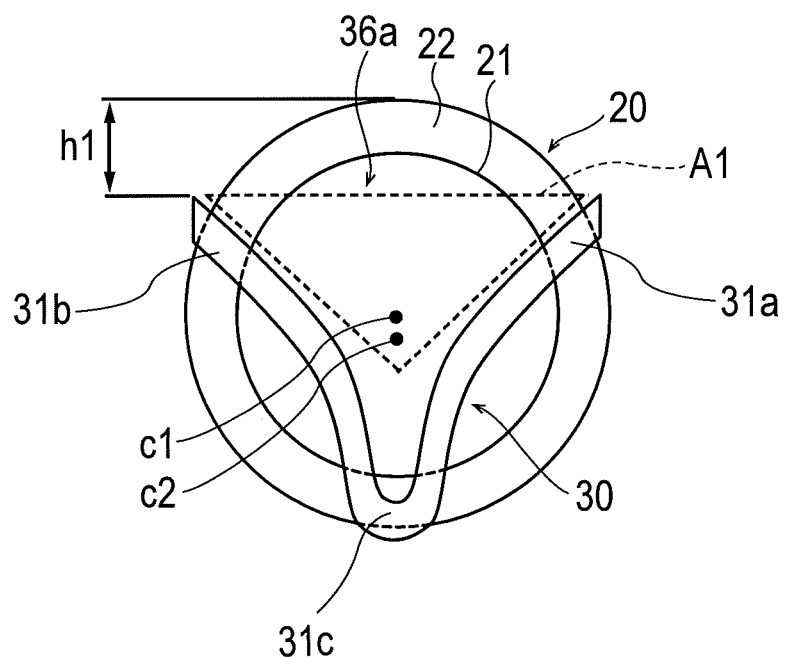
FIG. 3B is a front view of a distal member and the rotating member as viewed in a direction indicated by an arrow mark 3B of FIG. 2A.
Figure 4A:
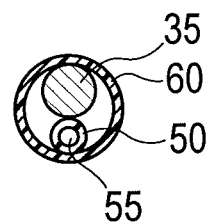
FIG. 4A is a sectional view taken along line IVA-IVA of FIG. 2A.
Figure 4B:
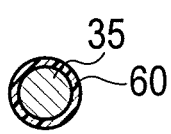
FIG. 4B is a sectional view taken along line IVB-IVB of FIG. 2A.
Figure 4C:
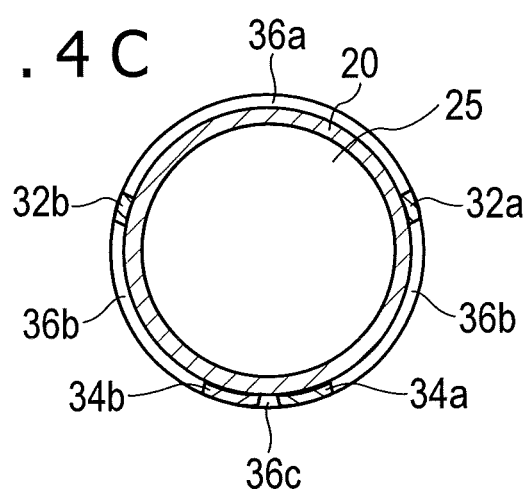
FIG. 4C is a sectional view taken along line IVC-IVC of FIG. 2A.
Figure 4D:
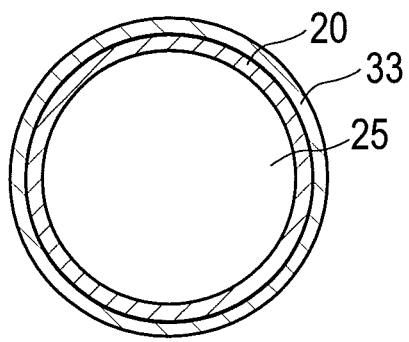
FIG. 4D is a sectional view taken along line IVD-IVD of FIG. 2A.
Figure 5A:
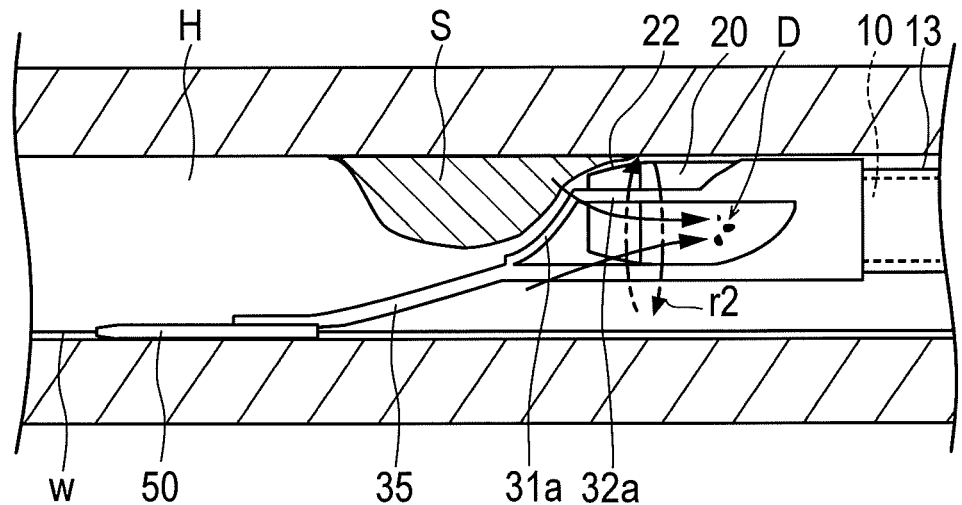
FIG. 5A is a sectional view schematically depicting an example of use of the medical device according to the embodiment.
Figure 5B:
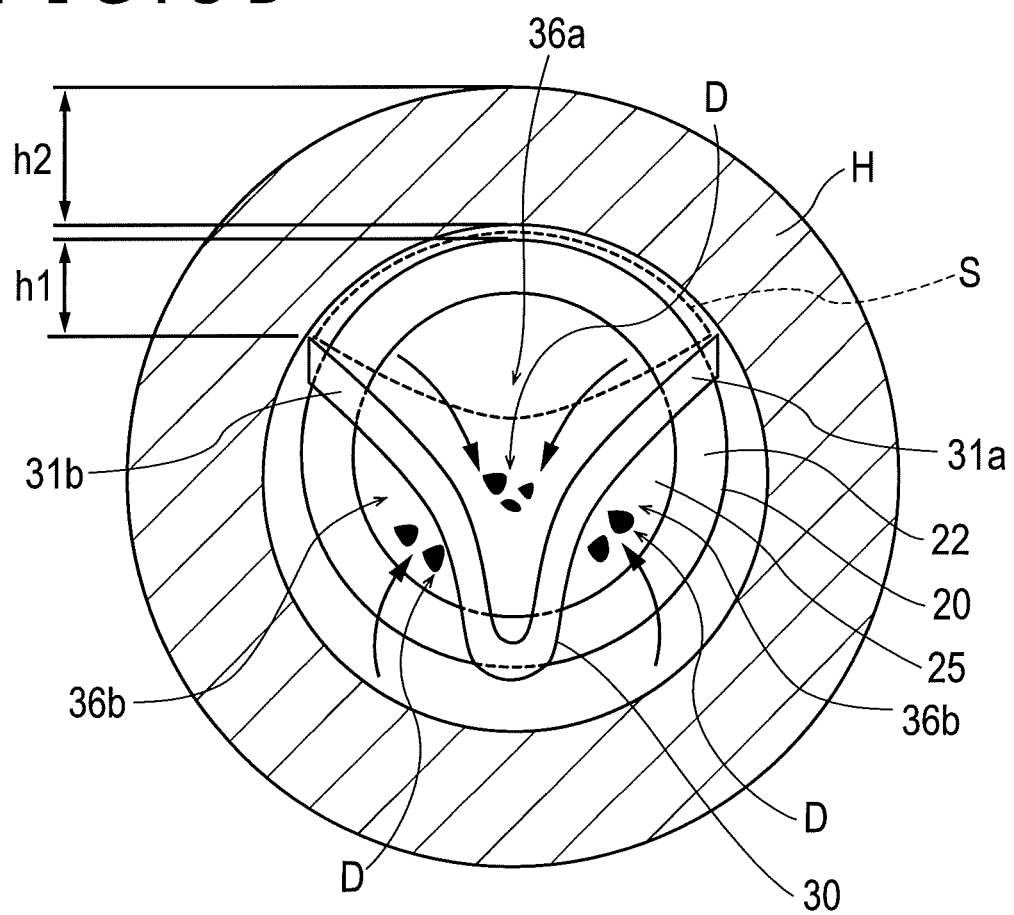
FIG. 5B is a cross sectional view schematically depicting the example of use of the medical device according to the embodiment.

FIGS. 1 to 4D depict a configuration of a medical device 1 according to an embodiment of the present disclosure, and FIGS. 5A and 5B illustrate action of the medical device 1. Note that FIG. 1 depicts a general configuration of the medical device 1; FIGS. 2A and 2B depict a distal member 30 provided on the medical device 1 in an enlarged scale; FIG. 3A depicts a configuration of an elongate member 10 and a rotating member 20 provided on the medical device 1; FIG. 3B illustrates an arrangement relationship of a cutting portion 22 of the rotating member 20 and the distal member 30; and FIGS. 4A to 4D depict cross sections at different portions of the medical device 1.

The medical device 1 according to the present embodiment is configured as a medical device which can be used for a treatment of cutting an object such as a stenosis S or a blocked portion formed in a living body lumen as depicted in FIG. 5A. The description of the embodiment is directed to an example in which the medical device 1 is applied to a treatment for cutting the stenosis S formed in a blood vessel H, which is a living body lumen.

In the present specification, a side of the medical device 1 to be inserted into the blood vessel H is referred to as distal end side (distal side), and another side of the medical device 1 on which a hand operation portion 150 is disposed is referred to as proximal end side (proximal side).

To explain the configuration briefly with reference to FIG. 1, the medical device 1 has the rotatable elongate member 10 for being inserted into the blood vessel H, the rotating member 20 having the cutting portion 22 for cutting the stenosis S, the distal member 30 disposed on the distal end side of the elongate member 10, and the hand operation portion 150 disposed on the proximal end side of the elongate member 10.

Now, a configuration of the components is described.

As depicted in FIG. 1, the rotating member 20 is disposed on the distal end side of the elongate member 10 covered with a cover member 13. As depicted in FIG. 3A, the rotating member 20 has a hollow shape having a lumen 25 extending in an axial direction of the rotating member 20. Further, as depicted in FIG. 3B, the rotating member 20 has a substantially circular shape as viewed in front elevation.

In accordance with an exemplary embodiment, the cutting portion 22 provided on the rotating member 20 is configured from a trephine blade (annular blade having a thickness decreasing toward the distal end side) known in the medical field. Since the rotating member 20 has the cutting portion 22 configured from such a blade as just described, the rotating member 20 can be advanced smoothly into the stenosis S, and also in a case in which the stenosis S is a soft tissue, cutting of the stenosis S can be performed efficiently. Further, by adopting a smooth blade like a trephine blade, the safety for a normal tissue, a blood vessel wall and so forth can be increased.

The rotating member 20 can be configured, for example, from a known metal material or resin material, or ceramics having biocompatibility. As the metal material, for example, stainless steel, nickel titanium (titanium alloy), tungsten, cobalt-chrome, titanium and tungsten carbide are available. The rotating member 20 may be configured from an article to which a surface treatment such as a nitriding treatment for the surface of any of the metals mentioned above is applied to increase the hardness of the surface from that of the base metal. Note that the cutting portion 22 may be configured in a multilayer structure in which same or different metals are arranged in multilayers. As the resin material, for example, ABS (acrylonitrile, butadiene, styrene copolymer synthetic resin), polyethylene, polypropylene, nylon, PEEK (polyether ether ketone), polycarbonate, acryl, polyacetal, modified polyphenylene ether, acrylonitrile styrene and a material of any of the resin materials mentioned into which an additive such as glass fiber is contained to increase the strength.

In accordance with an exemplary embodiment, the shape, structure and so forth of the cutting portion 22 are not particularly restricted only if the cutting portion 22 can cut the stenosis S of a cutting target. For example, the cutting portion 22 can be configured from a blade of a serrated shape having notches on the distal end side. Where the cutting portion 22 is configured from a blade of such a shape as just described, the rotating member 20 can finely crush the stenosis S, and therefore, the cutting efficiency can be raised.

As depicted in FIG. 3A, a distal end portion of the elongate member 10 is inserted in the lumen 25 of the rotating member 20. The distal end portion of the elongate member 10 is fixed to a proximal end portion of the rotating member 20.

The elongate member 10 is configured from an elongated coil spring having a lumen 15 extending in an axial direction thereof. As the coil spring, a known coil spring made of, for example, a metal or a resin can be used. In addition, the elongate member 10 and the rotating member 20 can be fixed to each other by such a method as, for example, adhesion by a bonding agent, fusing, or welding taking the material into consideration.

The structure, material and so forth of the elongate member 10 are not restricted particularly only if the elongate member 10 can transmit rotational driving force from the proximal end side to the distal end side of the elongate member 10 (from the hand operation portion 150 side to the rotating member 20 side). In accordance with an exemplary embodiment, the elongate member 10 can be configured from a member other than a coil spring. For example, the elongate member 10 can be configured from a tube made of a resin and configured from a single layer or a plurality of layers, a tube made of a resin and having a reinforcing member such as a blade added thereto, a pipe made of a metal and having slit processing or spiral processing applied thereto, a metal shaft including a core member (core metal) and a reinforcing member fixed to the core member, or a like member.

In accordance with an exemplary embodiment, the elongate member 10 is covered with the predetermined cover member 13. The cover member 13 protects a living body tissue from the elongate member 10 in a living body. Further, the cover member 13 stops debris D (refer to FIG. 5A) generated by cutting of the stenosis S from flowing out from the lumen 15 of the elongate member 10. As the cover member 13, a hollow tube configured from a known resin material such as, for example, polyethylene, polypropylene or polyamide can be used.

As depicted in FIG. 1, the hand operation portion 150 has a hub 151, a connector portion 153 provided on the hub 151, and a port 155 provided on the connector portion 153.

As depicted in FIG. 1, the elongate member 10 extends through the hub 151 and is led out on the proximal end side of the hub 151 from a proximal end port 152. A valve body 157 for preventing fluid and so forth from leaking from the proximal port 152 is disposed at a proximal end portion of the hub 151. Meanwhile, the proximal end side of the cover member 13 which covers the elongate member 10 is inserted in the hub 151 and fixed at a predetermined position in the hub 151. The cover member 13 is not fixed (interlocked) to any of the elongate member 10 and the rotating member 20.

The connector portion 153 can be configured, for example, from a Y connector known in the medical field. In the port 155 provided in the connector portion 153, a three-way stopcock for operating circulation of fluid inside and outside of the port 155 is disposed. The port 155 can be interlocked, for example, to a suction apparatus 190 through a tube 191 through which fluid can circulate. The suction apparatus 190 can be configured, for example, from a known fluid suction pump, which can generate a negative pressure.

A proximal end portion of the elongate member 10 is configured for connection to an external driving apparatus 180 through a predetermined connector (not depicted). The external driving apparatus 180 can include a driving source configured from, for example, a known electric motor which generates driving force for rotating the elongate member 10.

If the external driving apparatus 180 is rendered operative to apply rotating force to the elongate member 10, the elongate member 10 rotates as indicated by an arrow mark r1 in FIG. 3A. When the elongate member 10 rotates, the rotating member 20 disposed at the distal end of the elongate member 10 rotates as indicated by an arrow mark r2 in FIG. 3A. By the rotation of the rotating member 20, cutting force can be applied to the stenosis S from the cutting portion 22 of the rotating member 20. Note that, since the cover member 13 is not fixed to any of the elongate member 10 and the rotating member 20, the cover member 13 does not rotate even when the elongate member 10 rotates.

Control of operation of the external driving apparatus 180 and the suction apparatus 190 can be carried out, for example, by a control unit not depicted. As the control unit, for example, a control unit configured from a known microcomputer including a CPU (central processing unit), a RAM (random access memory), a ROM (read only memory) and so forth can be used. Further, the control unit may be a control unit which is incorporated in, for example, the external driving apparatus 180 or the suction apparatus 190 or a control unit which is incorporated in an apparatus different from the external driving apparatus 180 or the suction apparatus 190 and transfers a control signal and so forth by wire communication or wireless communication with the apparatus 180 and 190.

The rotation direction of the rotating member 20 when a treatment is to be performed may be any of the clockwise direction and the counterclockwise direction. Alternatively, the rotating member 20 may be rotated alternately in the clockwise direction and the counterclockwise direction.

Now, the distal member 30 is described.

As depicted in FIGS. 2A and 2B, the distal member 30 has a guide portion 31, a supporting portion 32, a proximal portion 33, a bottom portion 34 and an interlock portion 35. The guide portion 31 is disposed on the distal end side of the rotating member 20 with a space g left from the rotating member 20. The supporting portion 32 supports the guide portion 31 and defines a dimension of the space g in an axial direction of the elongate member 10. The proximal portion 33 is provided on the proximal end side of the supporting portion 32. The bottom portion 34 is disposed on the bottom face side of the rotating member 20, and the interlock portion 35 extends to the distal end side of the bottom portion 34.

The proximal portion 33 is a portion provided on the proximal end side of the distal member 30 and is fixed to the cover member 13 as hereinafter described. The supporting portion 32 extends toward the distal end side from the proximal portion 33 and is disposed along a side face of the rotating member 20. The bottom portion 34 extends toward the distal end side from the proximal portion 33 and is disposed along a bottom face of the rotating member 20. The guide portion 31 extends toward the distal end side from the supporting portion 32 and is connected at a distal end portion thereof to the interlock portion 35.

In accordance with an exemplary embodiment, the proximal portion 33 has a hollow shape. As depicted in FIG. 3A, a proximal end portion of the rotating member 20, a distal end portion of the elongate member 10 and a distal end portion of the cover member 13 are inserted in the proximal portion 33. Note that, in FIG. 3A, the distal member 30 is indicated by a broken line in order to indicate the configuration in the distal member 30 clearly.

The proximal portion 33 of the distal member 30 is fixed to an outer circumferential face of a distal end portion of the cover member 13. The fixation may be performed, for example, by such a mechanical method as fitting or screwing, or may be performed by such a method as adhesion by a bonding agent, fusing or welding taking the materials of the distal member 30 and the proximal portion 33 into consideration.

The distal member 30 is fixed to the cover member 13 but is not fixed to any of the elongate member 10 and the rotating member 20. Further, as described hereinabove, the cover member 13 is not fixed to any of the elongate member 10 and the rotating member 20. Accordingly, even if the elongate member 10 rotates, the distal member 30 does not rotate similarly to the cover member 13.

As depicted in FIG. 2B, the guide portion 31 has a first guide portion 31a and a second guide portion 31b.

The first guide portion 31a and the second guide portion 31b have a distance therebetween, which gradually decreases toward the distal end side. Further, as depicted in FIG. 2A, the guide portions 31a and 31b have a shape curved such that the height thereof gradually decreases toward the interlock portion 35. The guide portions 31a and 31b are joined integrally on the distal end side with respect to the rotating member 20.

As depicted in FIG. 2B, the supporting portion 32 has a first supporting portion 32a and a second supporting portion 32b.

The first supporting portion 32a extends between the proximal portion 33 and the first guide portion 31a. Meanwhile, the second supporting portion 32b extends between the proximal portion 33 and the second guide portion 31b. As described hereinabove, the proximal portion 33 is fixed to the cover member 13. Accordingly, the first guide portion 31a is supported on (interlocked to) the cover member 13 through the first supporting portion 32a and the proximal portion 33, and the second guide portion 31b is supported on (interlocked to) the cover member 13 through the second supporting portion 32b and the proximal portion 33.

The first supporting portion 32a supports the first guide portion 31a on the cover member 13 in such a manner as described above to form the space g between the first guide portion 31a and the rotating member 20. Similarly, the second supporting portion 32b supports the second guide portion 31b on the cover member 13 to form the space g between the second guide portion 31b and the rotating member 20.

The spaces g are formed between proximal end portions (positions indicated by broken lines b in FIGS. 2A and 2B) of the guide portions 31a and 31b and a distal end 21 of the rotating member 20. Note that the size of the spaces g (length in an axial direction, height in a direction crossing with the axial direction), the shape of the spaces g and so forth are not restricted particularly only if cut stenosis pieces (for example, debris D) can be introduced into the lumen 25 of the rotating member 20 through the spaces g and can be changed.

The circumferential length of the first supporting portion 32a and the circumferential length of the second supporting portion 32b are smaller than the circumferential length of the rotating member 20 (outer diameters of the cutting portion 22 and a portion on the proximal end side with respect to the cutting portion 22).

As depicted in FIG. 2B, the bottom portion 34 has a first bottom portion 34a and a second bottom portion 34b.

In accordance with an exemplary embodiment, the distance between the first bottom portion 34a and the second bottom portion 34b gradually decreases toward the distal end side. The bottom portions 34a and 34b are joined integrally to each other on the distal end side with respect to the rotating member 20 and are interlocked to the interlock portion 35 disposed on the distal end side of the rotating member 20.

The rotating member 20 is held in a state sandwiched from three directions of the opposite face sides and the bottom face side by the supporting portions 32a and 32b disposed on the side face sides of the rotating member 20 and the bottom portions 34a and 34b disposed on the bottom face side of the rotating member 20. Therefore, when the rotating member 20 rotates, since the axis of rotation stabilizes, the rotating member 20 can be rotated smoothly. Further, even if the rotating member 20 and the elongate member 10 are brought out of fixation unintentionally, since the rotating member 20 can be held by the supporting portions 32a and 32b and the bottom portions 34a and 34b, the rotating member 20 can be prevented from dropping off. Further, the supporting portions 32a and 32b prevent the rotating member 20 from being inadvertently projecting on the distal end side of the rotating member 20 thereby to help prevent the rotating member 20 from excessively entering the stenosis S. Therefore, upon treatment, a normal tissue can be prevented from being damaged by the rotating member 20.

In accordance with an exemplary embodiment, as depicted in FIGS. 2A and 2B, the interlock portion 35 is curved such that it is gradually spaced apart from the rotating member 20 from the proximal end side toward the distal end side. A guide wire insertion portion 50 hereinafter described is disposed at the distal end of the interlock portion 35.

The interlock portion 35 is configured for deformation along a heightwise direction intersecting with the axial direction (along directions indicated by a double-sided arrow mark a1-a2 in FIG. 2A). This arises from the following reason.

Where the interlock portion 35 is configured for deformation in the heightwise direction, the interlock portion 35 can be deformed along the lumen of a guiding sheath which is used when the medical device 1 is introduced into a living body, and therefore, insertion of the distal member 30 into the guiding sheath can be performed smoothly. Further, when the interlock portion 35 is projected from a guiding sheath, if the interlock portion 35 is deformed in such a state as depicted in FIG. 2A, then the guide wire insertion portion 50 disposed on the distal end side of the interlock portion 35 is brought into contact with the blood vessel wall of the blood vessel H to elevate the distal member 30 (refer to FIG. 5A). By the elevation, the rotating member 20 held on the distal member 30 is positioned in the heightwise direction with respect to the stenosis S. Since the rotating member 20 is positioned with respect to the stenosis S, cutting of the stenosis S can be performed efficiently. Further, also it is possible to suitably prevent an ordinary tissue from being damaged by the rotating member 20.

In the present embodiment, the guide portion 31 (first guide portion 31*a* and second guide portion 31*b*), supporting portion 32 (first supporting portion 32*a* and second supporting portion 32*b*), proximal portion 33, bottom portion 34 (first bottom portion 34*a* and second bottom portion 34*b*) and interlock portion 35 the distal member 30 has are interlocked to each other. In other words, the distal member 30 is configured from a single member on which the portions 31, 32, 33, 34 and 35 are combined integrally.

Although the material configuring the distal member 30 is not restricted particularly, it is possible to use, for example, a known resin material or metal material. For example, materials similar to those exemplified as a material of the rotating member 20 as above can be used. Note that the portions 31, 32, 33, 34 and 35 of the distal member 30 described above may be configured from materials different from each other or arbitrary plural ones of the portions may be configured from a same material while the other portions are configured from a different material. Alternatively, the portions may be configured from the same material.

As described hereinabove, where the interlock portion 35 is configured for deformation in the heightwise direction, it is possible to configure, for example, the interlock portion 35 from a known elastically deformable metal material or resin material, a known shape memory metal or shape memory resin shaped in advance so as to be deformed in the heightwise direction, or a like material. As the shape memory metal, for example, a titanium alloy (Ti—Ni, Ti—Pd, or Ti—Nb—Sn) or a copper alloy can be used. Meanwhile, as the shape memory resin, for example, an acrylic resin, trans isoprene polymer, polynorbornene, styrene butadiene copolymer and polyurethane can be used.

As depicted in FIGS. 2A and 2B, the distal member 30 has a first opening portion 36*a* disposed on the upper face side and the distal end side of the rotating member 20, a second opening portion 36*b* disposed on the opposite face sides of the rotating member 20, and a third opening portion 36*c* disposed on the bottom face side of the rotating member 20.

The first opening portion 36*a* communicates the inside and the outside of the distal member 30 with each other on the upper face side and the distal end side of the rotating member 20. The second opening portion 36*b* communicates the inside and the outside of the distal member 30 with each other on the side face sides of the rotating member 20. The third opening portion 36*c* communicates the inside and the outside of the distal member 30 with each other on the bottom face side of the rotating member 20.

As depicted in FIGS. 2A and 2B, the guide wire insertion portion 50 having a guide wire lumen 55 is disposed on the distal end side of each of the guide portions 31*a* and 31*b* (distal end side of the distal member 30).

The guide wire insertion portion 50 is configured from a hollow member extending in an axial direction. A distal end portion of the guide wire insertion portion 50 has a tapering shape, which tapers toward the distal end side in order to make it possible for the distal end portion to smoothly move in the blood vessel H. Note that there is no restriction to the shape, length, outer diameter, inner diameter, material and so forth of the guide wire insertion portion 50.

The guide wire insertion portion 50 is interlocked to the interlock portion 35. Although there is no particular restriction to the interlocking method, for example, it is possible to adopt such a method as to cover a proximal end portion of the guide wire insertion portion 50 and the interlock portion 35 with such a covering member (for example, a known heat shrinkable tube) 60 made of a resin as indicated by broken lines in FIGS. 2A and 2B and cause the covering member 60 to heat shrink so as to interlock the guide wire insertion portion 50 to the interlock portion 35. As the covering member 60, it is possible to use a hollow member configured from a fluororesin such as ETFE (ethylene-tetrafluoroethylene copolymer) or PTFE (polytetrafluoroethylene), polyolefin such as PE (polyethylene) or PP (polypropylene), polyamide, polyester or polyurethane.

Now, a relationship in magnitude of profiles (outer shapes in side elevation) of the portions of the distal member 30 is described with reference to FIGS. 4A to 4D. Note that FIG. 4A is a sectional view taken along line IVA-IVA of FIG. 2A; FIG. 4B is a sectional view taken along line IVB-IVB of FIG. 2A; FIG. 4C is a sectional view taken along line IVC-IVC of FIG. 2A; and FIG. 4D is a sectional view taken along line IVD-IVD of FIG. 2A.

As depicted in FIG. 4A, on the distal end side of the interlock portion 35, the interlock portion 35 and the guide wire insertion portion 50 are interlocked to each other by the covering member 60.

As depicted in FIG. 4B, the guide wire insertion portion 50 is not disposed on the proximal end side of the interlock portion 35. Therefore, the profile of the interlock portion 35 is smaller than the distal end portion of the interlock portion 35 depicted in FIG. 4A.

As depicted in FIG. 4C, at the location at which the supporting portion 32 (first supporting portion 32*a* and second supporting portion 32*b*) of the distal member 30 and the bottom portion 34 (first bottom portion 34*a* and second bottom portion 34*b*) of the distal member 30 hold the rotating member 20, the profile is greater than those at the portions depicted in FIGS. 4A and 4B by an influence of the outer diameter of the rotating member 20.

As depicted in FIG. 4D, at the location at which the rotating member 20 is held by the proximal portion 33 of the distal member 30, the profile is greater than those at the portions depicted in FIGS. 4A and 4B by an influence of the outer diameter of the rotating member 20.

Note that the relationship in magnitude of profiles at the portions of the distal member 30 can be changed in response to the shape of the distal member 30, the shape of the rotating member 20 and so forth. For example, the distal member 30 can be formed such that the profile of the distal member 30 gradually increases from the distal end side toward the proximal end side or such that the distal end side and the proximal end side have profiles of a similar size and an intermediate portion between them has a profile smaller than those at the other portions.

Now, a disposition relationship between the cutting portion 22 of the rotating member 20 and the guide portion 31 (first guide portion 31*a* and second guide portion 31*b*) is described with reference to FIG. 3B. Note that, in FIG. 3B, a front view as viewed in a direction of an arrow mark 3B in FIG. 2A is depicted in a simplified form.

As depicted in FIG. 3B, each of the guide portions 31*a* and 31*b* is disposed at a position at which it overlaps with part of the cutting portion 22 but exposes part of the cutting portion 22 as viewed from the distal end side of the distal member 30. In the present embodiment, the cutting portion 22 has a trephine blade disposed along a peripheral edge of the rotating member 20, and therefore, the guide portions 31*a* and 31*b* are disposed so as to overlap with the distal end 21 of the rotating member 20 together with part of the cutting portion 22.

The positional relationship between the guide portions 31*a* and 31*b* and the cutting portion 22 described above is maintained in a state in which external force is not applied to the distal member 30 as depicted in FIGS. 2A and 2B and in another state in which the guide portions 31a and 31b contact with the stenosis S as depicted in FIG. 5A. However, in the state in which no external force is applied and the state in which the guide portions 31a and 31b contact with the stenosis S, ranges over which the cutting portion 22 overlaps with the guide portions 31a and 31b and ranges within which the cutting portion 22 is exposed may be fixed or may be varied.

As depicted in FIG. 3B, the supporting portion 32 disposes, in a state in which no external force is applied, the center position c2 of the guide portion 31 (first guide portion 31a and second guide portion 31b) in the heightwise direction at a position displaced in the heightwise direction from the center position c1 of the rotating member 20 (center position of a cross section orthogonal to the axis). In the present embodiment, the center position c2 of the guide portion 31 in the heightwise direction is disposed such that it is displaced to the lower side in the heightwise direction with respect to the center position c1 of the rotating member 20. Note that the center position c2 of the guide portion 31 in the heightwise direction may be disposed so as to be displaced, for example, in the widthwise direction (leftward and rightward direction in FIG. 3B) with respect to the center position c1 of the rotating member 20, in both of the heightwise direction and the widthwise direction or in an oblique direction. Note that the heightwise direction is an example of a direction toward and away from the stenosis portion, and for example, where the stenosis S is formed at part of a circumferential direction (leftward and rightward direction in FIG. 5B) of the blood vessel H, the center positions c1 and c2 may each be displaced in the leftward and rightward direction with reference to the position at which the stenosis S is formed.

Each of the guide portions 31a and 31b is disposed such that it exposes the center position c1 of the rotating member 20 and overlaps at a plurality of locations with a circumferential edge of the rotating member 20 (portion of the rotating member 20 having the cutting portion 22). In the present embodiment, each of the guide portions 31a and 31b overlaps with a circumferential edge of the rotating member 20 at substantially symmetrical positions in a circumferential direction with reference to the center position c1 of the rotating member 20. Further, a connection portion 31c (refer to FIG. 2B) at which the guide portions 31a and 31b are connected to each other is disposed so as to overlap with a circumferential edge of the rotating member 20 at positions different from the positions at which the guide portions 31a and 31b overlap. In accordance with an exemplary embodiment, it is possible to provide a distance of, for example, 120 degrees in a circumferential direction between the first guide portion 31a, second guide portion 31b and connection portion 31c.

As depicted in FIG. 3B, the ratio (in area) of the portions at which the guide portions 31a and 31b and the cutting portion 22 overlap with each other in a circumferential direction as viewed from the distal end side of the distal member 30 is lower than that of the portions at which the cutting portion 22 is exposed from the guide portions 31a and 31b in a circumferential direction (portions at which the guide portions 31a and 31b and the cutting portion 22 do not overlap with each other).

Each of the guide portions 31a and 31b has a predetermined guide face A1 formed on the distal end side of the rotating member 20 with respect to the cutting portion 22. The guide face A1 prevents the rotating member 20 from moving in a direction away from the stenosis S (in the downward direction of the blood vessel H depicted in FIG. 5A) by supporting the rotating member 20 with respect to the stenosis S while the cutting portion 22 is contacted with the stenosis S to treat the stenosis S. Therefore, since the state in which the cutting portion 22 contacts with the stenosis S can be maintained, cutting can be performed efficiently.

Further, the guide face A1 limits the range in which the cutting portion 22 exerts cutting force (hereinafter referred to as effective cutting range) to a range of the portions at which the cutting portion 22 is exposed from the guide portions 31a and 31b (to a range of the height h1 depicted in FIG. 3B).

An advantage arising from setting an effective cutting range in such a manner as described above is described with reference to FIGS. 5A and 5B. FIGS. 5A and 5B schematically illustrate a manner when the medical device 1 is used to cut the stenosis S formed in the blood vessel H.

Upon cutting of the stenosis S, the rotating member 20 is rotated in such a manner as indicated by an arrow mark r2 in FIG. 5A. By moving the cutting portion 22 toward the stenosis S in the state in which the rotating member 20 is rotated, the stenosis S can be cut. For example, if the rotating member 20 unintentionally passes, while such a treatment as just described is performed, the stenosis S and reaches the blood vessel wall positioned on the upper side in FIG. 5A, a risk that the cutting portion 22 may penetrate (perforate) the blood vessel wall arises. As described hereinabove, if the effective cutting range is restricted by the guide face A1, then the risk that the cutting portion 22 may penetrate the blood vessel wall can be reduced significantly. Especially, by setting the effective cutting range such that the relationship between the height h1 of the effective cutting range and the thickness h2 of the blood vessel wall may be h2>h1 as depicted in FIG. 5B, it becomes possible to prevent penetration of the blood vessel wall with a higher degree of certainty.

When a manipulation is performed using the medical device 1 according to the present embodiment, the distal member 30 can be mounted on the medical device 1 in advance and prior to the manipulation. Therefore, preparing the guide face A1 does not have to be performed at a timing at which cutting is to be started. In addition, since the labor is not required for preparing the guide face A1 during the manipulation, and an occurrence of such a problem that a manipulation is progressed in a state in which the guide face A1 is not formed or ready can be prevented.

Note that, where the cutting efficiency by the cutting portion 22 is improved, while the balance between the cutting efficiency and the risk of penetration of a blood vessel wall is taken into consideration, for example, the shape of the rotating member 20 or the outer diameter of the cutting portion 22 is changed to perform such adjustment as to increase the effective cutting range. By performing such adjustment as just described, it becomes possible to achieve both an improvement of the cutting efficiency and an improvement of the safety of the medical device 1.

An example of a procedure of a manipulation in which the medical device 1 is used is described with reference to FIGS. 5A and 5B again.

Upon the manipulation, a guiding sheath (not depicted) is introduced to a location proximate to the stenosis S. The guiding sheath can be delivered to a location proximate to the stenosis S along a guide wire (not depicted), which has been introduced prior to the introduction of the guiding sheath. Note that, when the guiding sheath is delivered, use of the guide wire can be omitted.

Then, the medical device 1 is delivered to a location proximate to the stenosis S through the guiding sheath. Thereupon, a guide wire W is inserted into the guide wire insertion portion 50. The medical device 1 can be delivered to a location proximate to the stenosis S along the guide wire W.

If the distal member 30 is projected from the guiding sheath, the interlock portion 35 is deformed so as to extend in the heightwise direction (upward and downward direction in FIG. 5A) as depicted in FIG. 5A until the guide wire insertion portion 50 is brought into contact with the blood vessel wall. By the contact, the distal member 30 is raised to position the rotating member 20 with respect to the stenosis S.

Then, while the rotating member 20 is rotated as indicated by the arrow mark r2, the medical device 1 is pressed from the distal end side against the stenosis S. As cutting force is applied from the cutting portion 22 to the stenosis S, the stenosis substance included in the stenosis S (for example, plaque or a thrombus) can be scraped off.

In order to rotate the cutting portion 22 to scrape off the stenosis substance of the stenosis S, for example, the suction apparatus 190 depicted in FIG. 1 can be operated to suck the scraped off stenosis substance (debris) D into the lumen 25 of the rotating member 20. As depicted in FIG. 5B, the debris D flow into the lumen 25 of the rotating member 20 past the spaces g disposed on the distal end side of the rotating member 20 the opening portions 36a, 36b and 36c (refer to FIG. 2B) of the distal member 30. Further, the debris D are collected by the suction apparatus 190 through the lumen 15 of the elongate member 10 which communicates with the proximal end side of the rotating member 20. Thereupon, since the suction force for sucking in the debris D increases by convections generated by the rotation of the rotating member 20, the debris D move smoothly toward the lumen 25 of the rotating member 20.

The work for pressing the cutting portion 22 of the rotating member 20 against the stenosis S is continued and the medical device 1 is moved to the distal end side (left side in FIG. 5A). By performing this work, cutting can be performed along a direction in which the stenosis S extends. After it is confirmed that the cutting treatment for the stenosis S is completed, the medical device 1 is pulled out to the outside of the living body. Note that also it is possible to continuously carry out a treatment for a different stenosis S.

Now, operation of the present embodiment is described.

The medical device 1 according to the present embodiment can include the rotatable elongate member 10, the rotating member 20 having the cutting portion 22 for cutting a stenosis S and disposed on the distal end side of the elongate member 10 such that it rotates together with rotation of the elongate member 10, the guide portion 31 disposed on the distal end side of the rotating member 20 with a space g left from the rotating member 20, and the distal member 30 having the supporting portion 32 which supports the guide portion 31 and defines the dimension of the space g in an axial direction of the elongate member 10. The guide portion 31 is disposed at a position at which it overlaps with part of the cutting portion 22 and exposes part of the cutting portion 22 as viewed from the distal end side of the distal member 30.

With the medical device 1 configured in such a manner as described above, when it cuts the stenosis S, the guide portion 31 disposed on the distal end side of the rotating member 20 restricts a range within which the cutting portion 22 can cut (range within which the cutting portion 22 and the stenosis S contact with each other). Therefore, even if such a situation occurs that the rotating member 20 reaches the blood vessel wall of the blood vessel H during a treatment, the rotating member 20 can be prevented from penetrating the blood vessel wall.

Further, the rotating member 20 has a hollow shape having the lumen 25, and the medical device 1 collects at least part of debris D cut by the cutting portion 22 into the lumen 25 of the rotating member 20 through the space g. Since the medical device 1 is configured in this manner, while the guide portion 31 helps prevent the blood vessel wall from being penetrated, the debris D can be collected by the lumen 25 of the rotating member 20 through the space g. Therefore, the safety when a treatment is performed and the collection efficiency of the debris D can be increased.

Further, the supporting portion 32 disposes the center position c2 in the heightwise direction of the guide portion 31 at a position displaced in the heightwise direction from the center position c1 in the heightwise direction of the rotating member 20 in a state in which no external force is applied. By setting the relationship between the center position c1 in the heightwise direction of the rotating member 20 and the center position c2 in the heightwise direction of the guide portion 31 in this manner, the ratio between the range within which the guide portion 31 overlaps with the cutting portion 22 of the rotating member 20 and the range within which the cutting portion 22 of the rotating member 20 is exposed from the guide portion 31 can be readily adjusted. Consequently, the height h1 of the effective cutting range can be set to an appropriate magnitude.

Further, each of the guide portions 31a and 31b is disposed such that it exposes the center position c1 of the rotating member 20 and overlaps at a plurality of portions with a circumferential edge of the rotating member 20 as viewed from the distal end side of the distal member 30. Therefore, the cutting portion 22 of the rotating member 20 can be exposed from the guide portion 31 over a comparatively wide range including the center position c1 of the rotating member 20, and consequently, the cutting efficiency can be improved.

Further, the ratio of a region in which the guide portions 31a and 31b and the cutting portion 22 overlap with each other in a circumferential direction as viewed from the distal end side of the distal member 30 is lower than that in a region in which the cutting portion 22 is exposed from the guide portions 31a and 31b in a circumferential direction. Therefore, the cutting efficiency is further improved.

Further, since the outer circumferential length of the first supporting portion 32a and the outer circumferential length of the second supporting portion 32b are smaller than the outer circumferential length of the rotating member 20, the distal member 30 can be compact.

Further, the cover member 13 is provided on the medical device 1 such that it covers at least part of the elongate member 10 and is disposed so as not to rotate in an interlocking relationship with rotation of the rotating member 20. The distal member 30 is connected to the cover member 13 such that it does not rotate in an interlocking relationship with rotation of the rotating member 20. Therefore, since the distal member 30 can be prevented from rotating inadvertently while a cutting work is being performed by the rotating member 20, the manipulation can be smoothly performed.

Further, the distal member 30 has the guide portion 31 and the supporting portion 32 configured integrally with each other. Since the guide portion 31 and the supporting portion 32 are configured integrally, attachment of the medical device 1 to the cover member 13 can be readily performed.

Further, the medical device 1 can include the guide wire lumen 55 into which the guide wire W can be inserted and has the guide wire insertion portion 50 attached to the distal end side thereof with respect to the guide portion 31. Therefore, an operation for delivering the medical device 1 into the blood vessel H and an operation for moving the medical device 1 in the blood vessel H making use of the guide wire W can be performed. Therefore, a smooth manipulation can be implemented.

Now, modifications to the distal member 30 described in connection with the embodiment are described. Note that any configuration not mentioned particularly in the description of the modifications is similar to that in the embodiment described above. Further, like members to those described above are denoted by like reference characters and overlapping description of the like members and also of like members applied in the modifications is omitted herein to avoid redundancy.

Figure 6A:
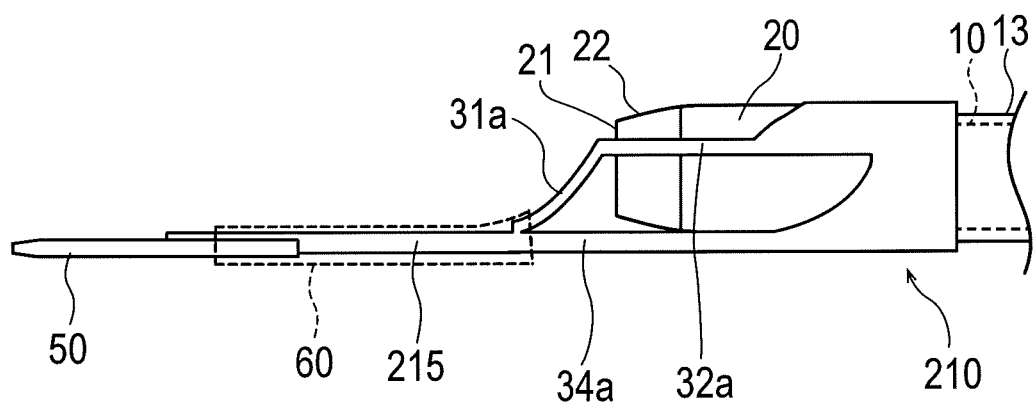
FIG. 6A is a lateral view depicting a distal member according to a modification 1 to the embodiment.
Figure 6B:
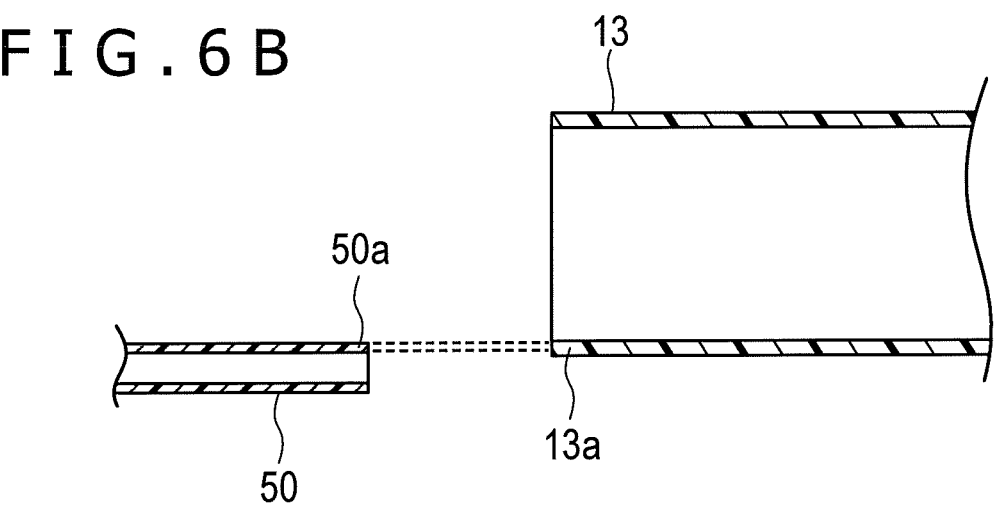
FIG. 6B is a view briefly illustrating a positional relationship between a guide wire insertion portion and a cover member according to the modification 1.

FIG. 6A is a lateral view depicting a distal member 210 according to a modification 1, and FIG. 6B is a view illustrating a positional relationship between a guide wire insertion portion 50 and a cover member 13 in a simplified form.

In the embodiment described above, the interlock portion 35 provided on the distal member 30 is shaped such that it is curved so as to be gradually spaced apart from the rotating member 20 from the proximal end side toward the distal end side (refer to FIG. 2A). In contrast, in the present modification, an interlock portion 215 extends substantially linearly along an axial direction of the distal member 210. Where the connection portion 215 has such a shape as just described, the medical device 1 can be further reduced in diameter, and therefore, the delivery performance of the medical device 1 can be improved. Further, for example, by disposing a pipe wall 50a on the upper face side of the guide wire insertion portion 50 and a pipe wall 13a on the lower face side of the cover member 13, which covers the elongate member 10, so as to overlap with each other in the thicknesswise direction (heightwise direction) of them as depicted in FIG. 6B, further reduction in diameter of the medical device 1 can be anticipated. Note that, if the guide wire insertion portion 50 and the cover member 13 have such a disposition relationship as just described, then also interference between the guide wire W inserted in the guide wire insertion portion 50 and the cover member 13 can be prevented.

Figure 7A:
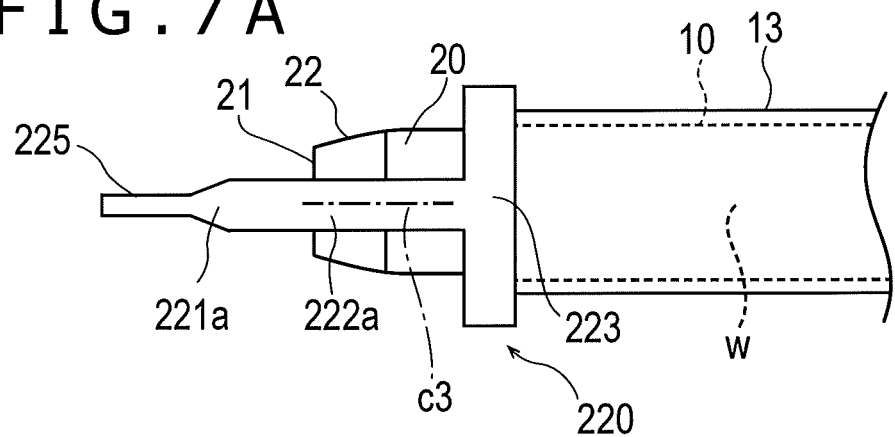
FIG. 7A is a lateral view depicting a distal member according to a modification 2 to the embodiment.
Figure 7B:
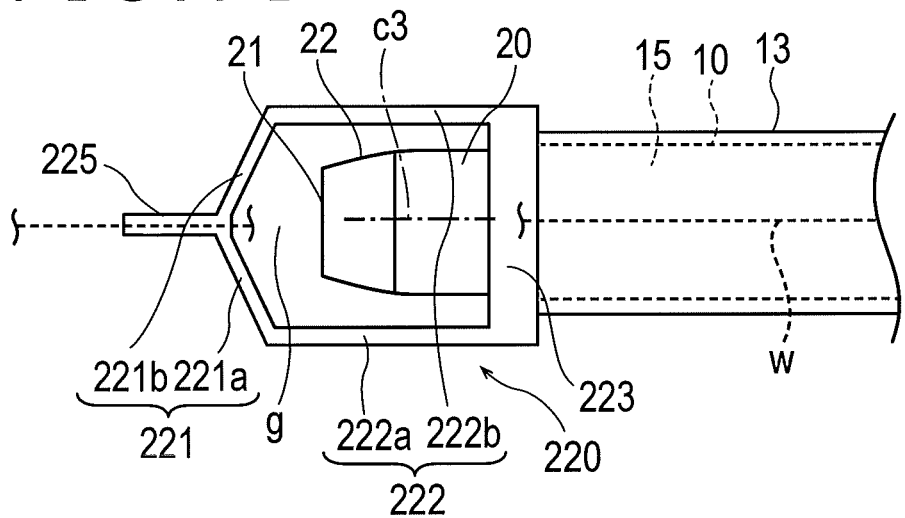
FIG. 7B is a plan view depicting the distal member according to the modification 2 to the embodiment.
Figure 7C:
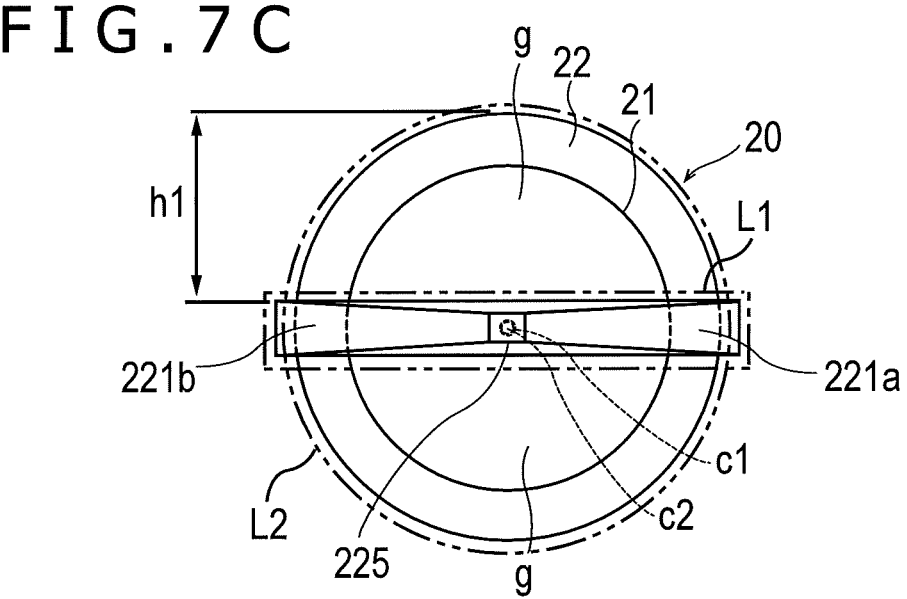
FIG. 7C is a front view depicting the distal member according to the modification 2 to the embodiment.

FIG. 7A is a lateral view depicting a distal member 220 according to a modification 2, and FIGS. 7B and 7C are a plan view and a front view depicting the distal member 220 according to the modification 2, respectively.

The distal member 220 according to the present modification has a guide portion 221, a supporting portion 222 disposed on the proximal end side of the guide portion 221 and supporting the guide portion 221 thereon, a proximal portion 223 disposed on the proximal end side of the supporting portion 222 and fixed to the cover member 13, and an extension 225 extending substantially linearly on the distal end side of the guide portion 221.

The guide portion 221 has a first guide portion 221a and a second guide portion 221b branching symmetrically bifurcatedly from the axis c3 of the rotating member 20.

The supporting portion 222 has a first supporting portion 222a disposed between the first guide portion 221a and the proximal portion 223, and a second supporting portion 222b disposed between the second guide portion 221b and the proximal portion 223.

As depicted in FIG. 7C, the guide portion 221 is disposed such that the center position c2 of the guide portion 221 in the heightwise direction overlaps with the center position c1 in the heightwise direction of the rotating member 20. Further, the ratio of a region in which each of the guide portions 221a and 221b and the cutting portion 22 overlap with each other in a circumferential direction as viewed from the distal end side of the distal member 220 is lower than that in a region in which the cutting portion 22 is exposed from each of the guide portions 221a and 221b in a circumferential direction.

The guide portion 221 and the rotating member 20 have shapes different from each other as viewed from the distal end side of the distal member 30, and the outer circumferential length L1 of the guide portion 221 is shorter than the outer circumferential length L2 of the rotating member 20. Note that the guide portion 221 has a rectangular shape elongated in the widthwise direction as viewed from the distal end side of the distal member 30 as depicted in FIG. 7C.

The proximal portion 223 is disposed so as to cover the outer periphery of a distal end portion of the cover member 13 and is fixed to the cover member 13 in a state in which it covers the outer periphery.

The extension 225 disposed on the distal end side of the guide portion 221 has a function for enhancing the delivery performance of the medical device 1 when the medical device 1 is moved in the blood vessel H. Note that also it is possible, for example, to dispose a guide wire lumen in the extension 225 and utilize the extension 225 as a guide wire insertion portion. The guide wire W may be, for example, inserted in the lumen 15 of the elongate member 10 as indicated by a broken line in FIG. 7B, or may be inserted into the extension 225 from the circumference of the elongate member 10 without inserting the guide wire W into the lumen 15 of the elongate member 10.

As depicted in FIG. 7C, the first guide portion 221a and the second guide portion 221b of the distal member 220 limit the effective cutting range to a range of the height h1. Accordingly, by proving the distal member 220 according to the present modification on the medical device 1, the rotating member 20 can be prevented from penetrating a blood vessel wall while a treatment is being performed. Further, when a treatment is performed using the distal member 220 of the present modification, since the debris D can be collected through the space g disposed on the upper face side and the lower face side of the rotating member 20, the collection efficiency of the debris D can be improved.

Figure 8A:
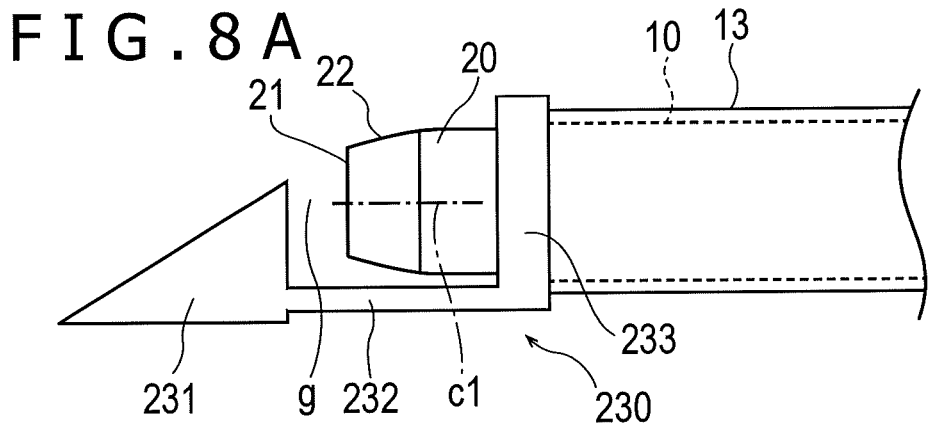
FIG. 8A is a lateral view depicting a distal member according to a modification 3 to the embodiment.
Figure 8B:
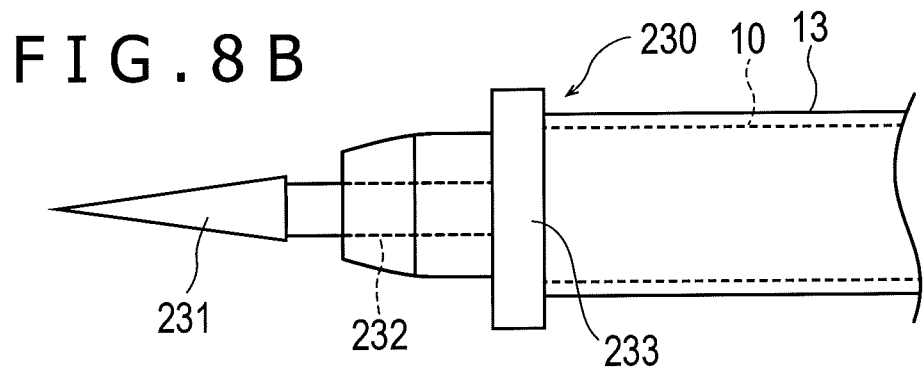
FIG. 8B is a plan view depicting the distal member according to the modification 3 to the embodiment.
Figure 8C:
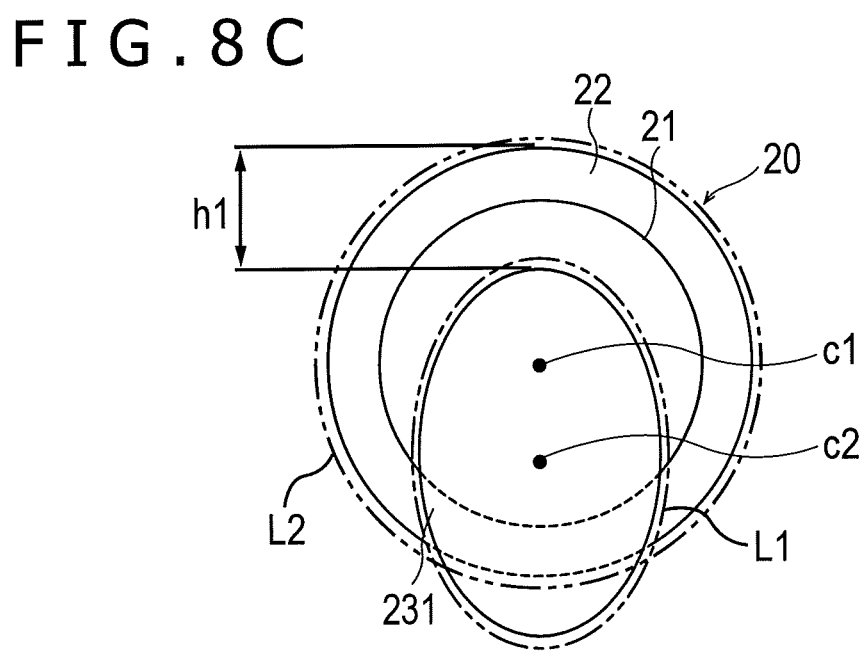
FIG. 8C is a front view depicting the distal member according to the modification 3 to the embodiment.

FIGS. 8A, 8B, and 8C are a lateral view, a plan view and a front view depicting a distal member 230 according to a modification 3, respectively.

The distal member 230 according to the present modification has a guide portion 231, a supporting portion 232 disposed on the proximal end side of the guide portion 231 and supporting the guide portion 231 thereon, and a proximal portion 233 disposed on the proximal end side of the supporting portion 232 and fixed to the cover member 13.

The supporting portion 232 disposes, in a state in which no external force is applied thereto, the center position c2 in the heightwise direction of the guide portion 231 at a position displaced in the heightwise direction from the center position c1 in the heightwise direction of the rotating member 20.

The guide portion 231 is disposed such that it overlaps with the center position c1 in the heightwise direction of the rotating member 20 and part of a circumferential edge of the rotating member 20 as viewed from distal end side of the distal member 230. Further, the guide portion 231 and the rotating member 20 have shapes different from each other as viewed from the distal end side of the distal member 230, and the outer circumferential length L1 of the guide portion 231 is shorter than the outer circumferential length L2 of the rotating member 20.

In accordance with an exemplary embodiment, the guide portion 231 has a substantially elliptical shape having a long axis disposed in the heightwise direction (in the upward and downward direction in FIG. 8C) and a short axis disposed in the widthwise direction (in the leftward and rightward direction in FIG. 8C) in a front view depicted in FIG. 8C. Further, the guide portion 231 is shaped such that the dimension in the heightwise direction of the guide portion 231 gradually decreases from the proximal end side toward the distal end side as depicted in FIG. 8A.

A portion of the cutting portion 22 other than a portion with which the guide portion 231 overlaps in the heightwise direction is exposed from the guide portion 231. In accordance with an exemplary embodiment, the cutting portion 22 is disposed such that a portion of the cutting portion 22 whose dimension in a short axis direction (in the leftward and rightward direction) is smaller than that of a portion at which the dimension is greatest overlaps with a circumferential edge of the rotating member 20. Therefore, the ratio of a region in which the guide portion 231 and the cutting portion 22 overlap with each other in a circumferential direction is lower than that in a region in which the cutting portion 22 is exposed from the guide portion 231 in a circumferential direction. Further, since the long axis of the guide portion 231 is disposed along the heightwise direction, the dimension of the distal member 230 in the widthwise direction can be prevented from becoming excessively great.

The supporting portion 232 is disposed on the bottom face side of the rotating member 20. The supporting portion 232 disposes, in a state in which no external force is applied thereto, the guide portion 231 at a position displaced in the heightwise direction from the center position c1 of the rotating member 20. Therefore, a proximal end portion of the guide portion 231 is disposed at a position displaced toward the bottom face side from the center position c1 of the distal end portion of the rotating member 20.

As depicted in FIG. 8C, the guide portion 231 of the distal member 230 can restrict the effective cutting range to the range of the height h1. Accordingly, by providing the distal member 230 according to the present modification on the medical device 1, the rotating member 20 can be prevented from penetrating the blood vessel wall while a treatment is being performed.

Further, since the supporting portion 232 disposes the center position c2 in the heightwise direction of the guide portion 231 at a position displaced in the heightwise direction from the center position c1 in the heightwise direction of the rotating member 20, a greater space g can be disposed between the guide portion 231 and the distal end of the rotating member 20. Accordingly, the debris D can be collected in a higher efficiency into the lumen 25 of the rotating member 20.

Further, since the guide portion 231 has a dimension in the heightwise direction smaller at a distal end portion than at a proximal end portion of the guide portion 231, the medical device 1 can be moved smoothly in the blood vessel H and the delivery performance can be improved further.

Further, the guide portion 231 is disposed such that it overlaps with the center position c1 in the heightwise direction of the rotating member 20 and part of a circumferential edge of the rotating member 20 as viewed from the distal end side of the distal member 230. Therefore, since the function for guiding the movement of the medical device 1 on the distal end side of the rotating member 20 can be enhanced, the delivery performance can be further improved.

Further, the guide portion 231 and the rotating member 20 have shapes different from each other as viewed from the distal end side of the distal member 230, and the outer circumferential length L1 of the guide portion 231 is shorter than the outer circumferential length L2 of the rotating member 20. Therefore, a region in which the guide portion 231 and the cutting portion 22 overlap with each other and another region in which the cutting portion 22 is exposed from the guide portion 231 can be provided with a relative higher degree of certainty.

Figure 9A:
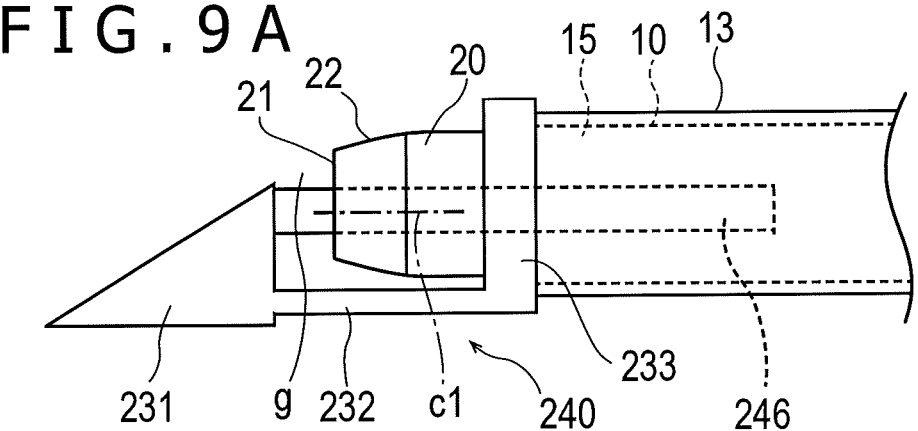
FIG. 9A is a lateral view depicting a distal member according to a modification 4 to the embodiment.
Figure 9B:
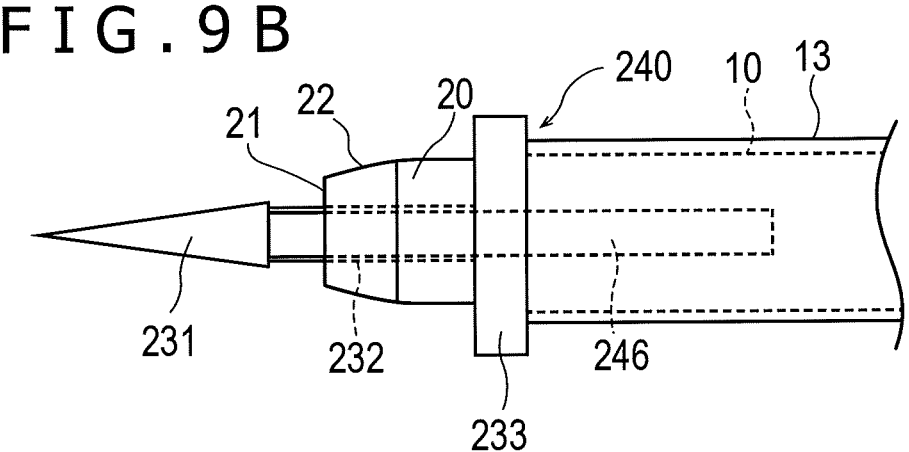
FIG. 9B is a plan view depicting the distal member according to the modification 4 to the embodiment.
Figure 9C:
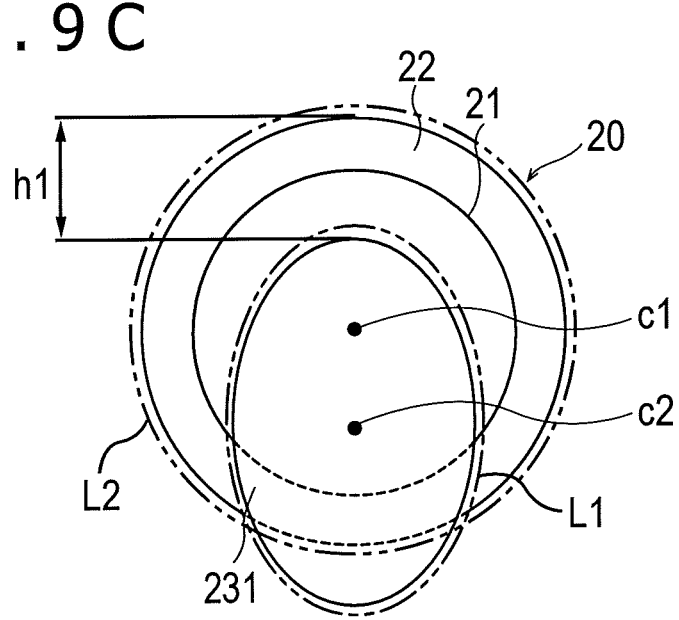
FIG. 9C is a front view depicting the distal member according to the modification 4 to the embodiment.

FIGS. 9A, 9B, and 9C are a lateral view, a plan view and a front view depicting a distal member 240 according to a modification 4, respectively.

The distal member 240 according to the present modification has a shape substantially same as that of the distal member 230 according to the modification 3 described above. However, the distal member 240 is different from the distal member 230 described above in that it can include a connection member 246 connecting to the guide portion 231.

The connection member 246 is connected at the distal end side of the connection member 246 to a proximal end face of the guide portion 231 and is inserted on the proximal end side of guide portion 231 in the lumen 15 of the elongate member 10. The connection member 246 can be configured, for example, from a known resin material or metal material. The connection member 246 is not particularly limited in sectional shape or length dimension and may be a hollow member or a solid member.

Similarly to the modifications described above, the supporting portion 232 is provided such that, in a state in which no external force is applied thereto, the center position c2 in the heightwise direction of the guide portion 231 is disposed at a position displaced in the heightwise direction from the center position c1 in the heightwise direction of the rotating member 20. The guide portion 231 is disposed such that it overlaps with the center position c1 in the heightwise direction of the rotating member 20 and part of a circumferential edge of the rotating member 20 as viewed from the distal end side of the distal member 240. Further, the outer circumferential length L1 of the guide portion 231 is shorter than the outer circumferential length L2 of the rotating member 20.

The cutting portion 22 is exposed, at a portion thereof other than a portion with which the guide portion 231 overlaps in the heightwise direction, from the guide portion 231. In accordance with an exemplary embodiment, the cutting portion 22 is disposed such that a portion of the cutting portion 22 whose dimension in a short axis direction (in the leftward and rightward direction) is smaller than that of a portion at which the dimension is greatest overlaps with a circumferential edge of the rotating member 20. Therefore, the ratio of a region in which the guide portion 231 and the cutting portion 22 overlap with each other in a circumferential direction is lower than that of a region in which the cutting portion 22 is exposed from the guide portion 231 in a circumferential direction.

In the distal member 240 in the present modification, also when, for example, the supporting portion 232 or the proximal portion 233 is damaged, since the connection between the guide portion 231 and the elongate member 10 is maintained by the connection member 246, exposure of the cutting portion 22 of the rotating member 20 can be prevented even at a curved portion of the blood vessel H. Further, the function of the guide portion 231 can be prevented from being damaged.

Figure 10A:
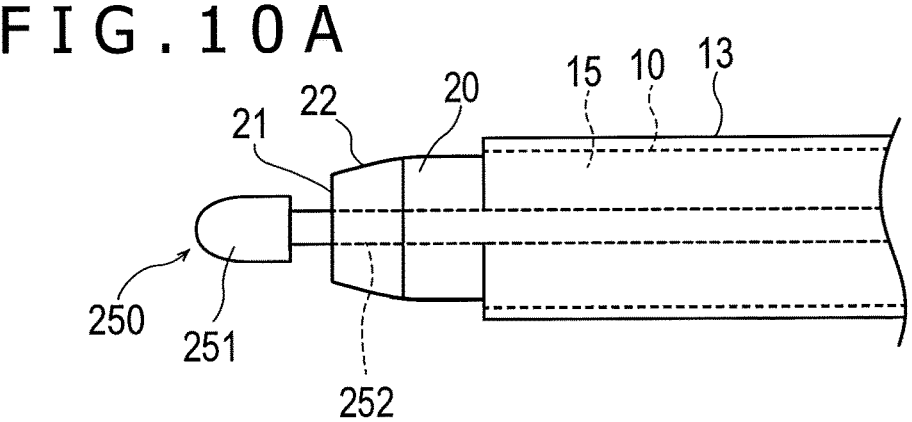
FIG. 10A is a lateral view depicting a distal member according to a modification 5 to the embodiment.
Figure 10B:
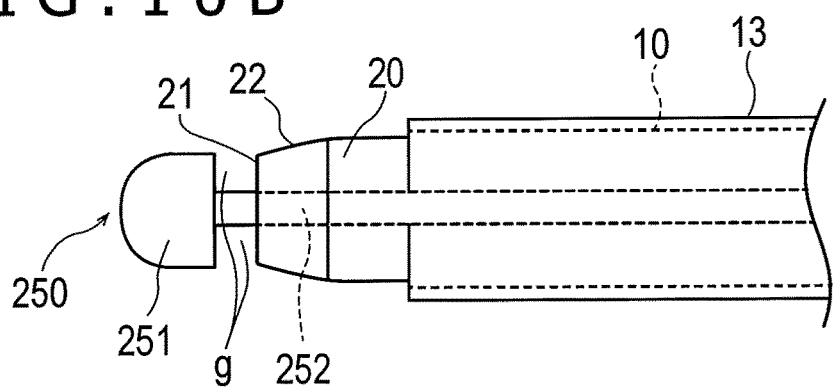
FIG. 10B is a plan view depicting the distal member according to the modification 5 to the embodiment.
Figure 10C:
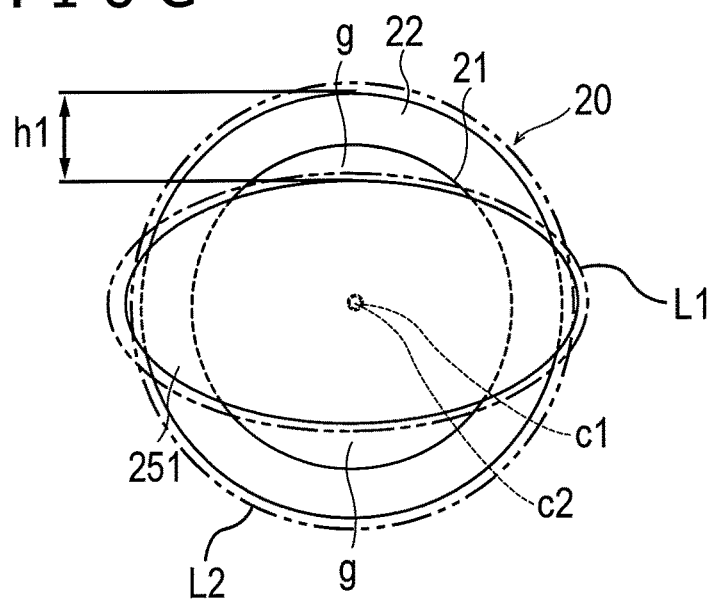
FIG. 10C is a front view depicting the distal member according to the modification 5 to the embodiment.

FIGS. 10A, 10B, and 10C are a lateral view, a plan view and a front view depicting a distal member 250 according to a modification 5, respectively.

The distal member 250 according to the present modification has a guide portion 251, and a supporting portion 252 disposed on the proximal end side of the guide portion 251 and supporting the guide portion 251 thereon. The supporting portion 252 is inserted in the lumen 15 of the elongate member 10 and is fixed in the inside of the hub 151 (refer to FIG. 1) provided on the hand operation portion 150.

The guide portion 251 has, as viewed in front elevation depicted in FIG. 10C, a substantially elliptical shape having a short axis disposed in the heightwise direction (upward and downward direction in FIG. 10C) and a long axis disposed in the widthwise direction (leftward and rightward direction in FIG. 10C). Further, the guide portion 251 is shaped such that the dimension thereof in the heightwise direction gradually decreases from a proximal end portion toward a distal end portion while being curved as depicted in FIG. 10A.

As depicted in FIG. 10C, the guide portion 251 is disposed such that the center position $c2$ in the heightwise direction of the guide portion 251 overlaps with the center position $c1$ in the heightwise direction of the rotating member 20. A region of the cutting portion 22 other than a portion with which the guide portion 251 overlaps in the heightwise direction is exposed from the guide portion 251. In accordance with an exemplary embodiment, the guide portion 251 is disposed such that a portion thereof whose dimension along a long axis direction (leftward and rightward direction) is greatest overlaps with a circumferential edge of the rotating member 20.

As depicted in FIG. 10C, the guide portion 251 of the distal member 250 limits the effective cutting range to the range of the height h1. Accordingly, by providing the distal member 250 according to the present modification on the medical device 1, it is possible to help prevent the rotating member 20 from penetrating the blood vessel wall while a treatment is being performed. Further, when a treatment is to be performed by the distal member 250 of the present modification, since the debris D can be collected through the space g disposed on the upper face side and the lower face side of the rotating member 20, the collection efficiency of the debris D can be improved.

Figure 11A:
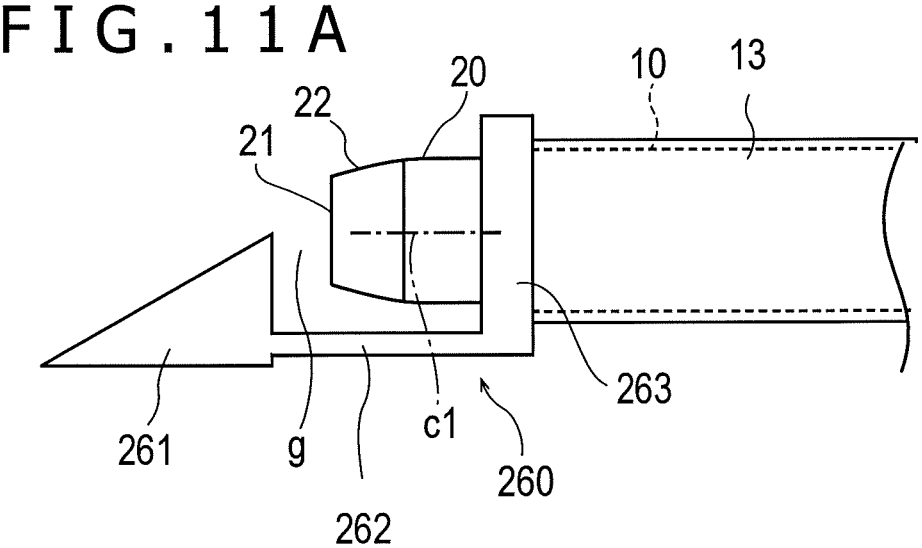
FIG. 11A is a lateral view depicting a distal member according to a modification 6 to the embodiment.
Figure 11B:
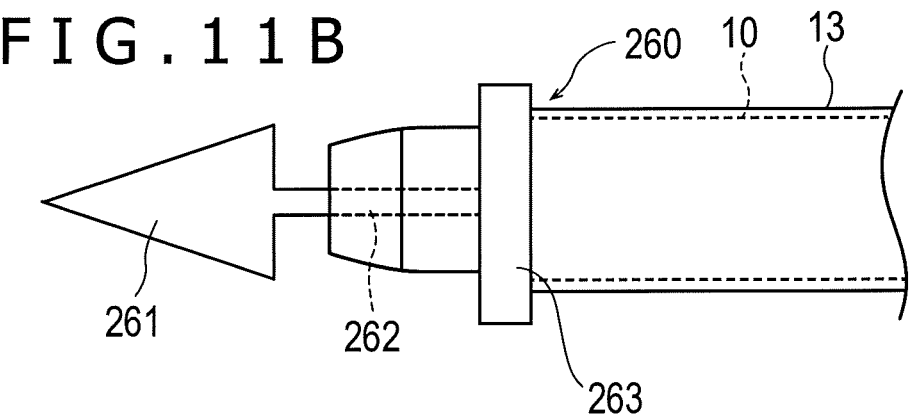
FIG. 11B is a plan view depicting the distal member according to the modification 6 to the embodiment.
Figure 11C:
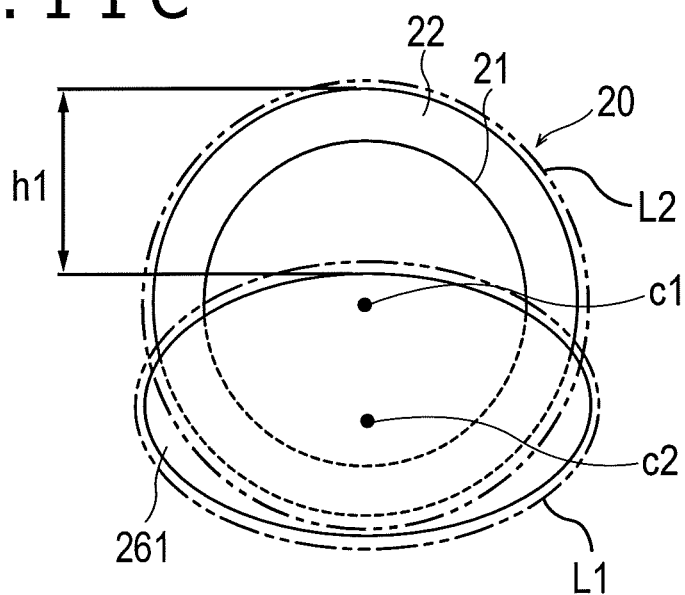
FIG. 11C is a front view depicting the distal member according to the modification 6 to the embodiment.

FIGS. 11A, 11B, and 11C are a lateral view, a plan view and a front view depicting a distal member 260 according to a modification 6, respectively.

The distal member 260 according to the present modification has a guide portion 261, a supporting portion 262 disposed on the proximal end side of the guide portion 261 and supporting the guide portion 261 thereon, and a proximal portion 263 disposed on the proximal end side of the supporting portion 262 and fixed to the cover member 13.

The guide portion 261 has, as viewed in front elevation depicted in FIG. 11C, a substantially elliptical shape having a short axis disposed in the heightwise direction (upward and downward direction in FIG. 11C) and a long axis disposed in the widthwise direction (leftward and rightward direction in FIG. 11C). Further, the guide portion 261 is shaped such that the dimension thereof in the heightwise direction gradually decreases from a proximal end portion toward a distal end portion as depicted in FIG. 11A.

As depicted in FIG. 11C, in a state in which no external force is applied, the supporting portion 262 disposes the center position $c2$ in the heightwise direction of the guide portion 261 at a position displaced in the heightwise direction from the center position $c1$ in the heightwise direction of the rotating member 20.

Further, the guide portion 261 is disposed such that it overlaps with the center position $c1$ in the heightwise direction of the rotating member 20 and part of a circumferential edge of the rotating member 20 as viewed from the distal end side of the distal member 260. A portion of the cutting portion 22 other than a portion with which the guide portion 261 overlaps in the heightwise direction is exposed from the guide portion 261. In accordance with an exemplary embodiment, the guide portion 261 is disposed such that a portion thereof whose dimension along a long axis direction (leftward and rightward direction) is greatest overlaps with a circumferential edge of the rotating member 20.

As depicted in FIG. 11C, the guide portion 261 of the distal member 260 limits the effective cutting range to the range of the height h1. Accordingly, by providing the distal member 260 according to the present modification on the medical device 1, the rotating member 20 can be prevented from penetrating the blood vessel wall while a treatment is being performed.

Figure 12:
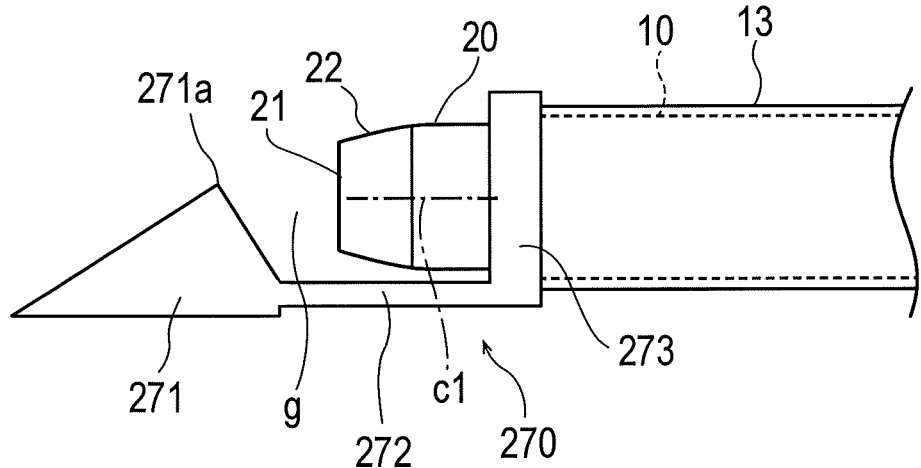
FIG. 12 is a lateral view depicting a distal member according to a modification 7 to the embodiment.

FIG. 12 is a lateral view depicting a distal member 270 according to a modification 7.

The distal member 270 according to the present modification has a guide portion 271, a supporting portion 272 disposed on the proximal end side of the guide portion 271 and supporting the guide portion 271 thereon, and a proximal portion 273 disposed on the proximal end side of the supporting portion 272 and fixed to the cover member 13.

As indicated by the present modification, the shape of the guide portion 271 laterally can be set to a substantially triangular shape in which a vertex 271a at which the dimension in the heightwise direction is in the maximum is displaced to the proximal end side. Where the guide portion 271 is configured in this manner, since the distal end portion side of the guide portion 271 is disposed at an acute angle, the medical device 1 can move more smoothly in the blood vessel H. Therefore, the delivery performance of the medical device 1 can be further improved.

Figure 13:
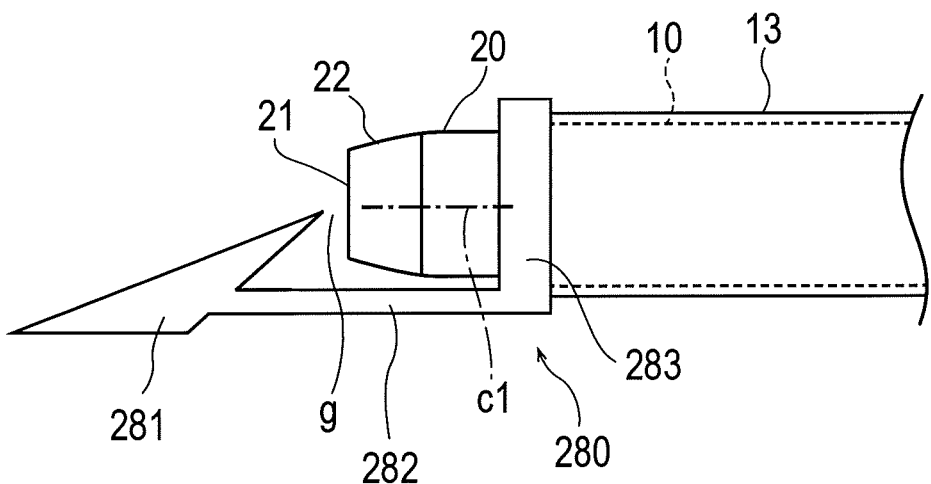
FIG. 13 is a lateral view depicting a distal member according to a modification 8 to the embodiment.

FIG. 13 is a lateral view depicting a distal member 280 according to a modification 8.

The distal member 280 according to the present modification has a guide portion 281, a supporting portion 282 disposed on the proximal end side of the guide portion 281 and supporting the guide portion 281 thereon, and a proximal portion 283 disposed on the proximal end side of the supporting portion 282 and fixed to the cover member 13.

The distal end portion side of the distal end portion of the guide portion 281 according to the present modification has an acuter angle than that of the guide portion 271 described hereinabove in connection with the modification 7. Therefore, the delivery performance of the medical device 1 is further improved.

Figure 14:
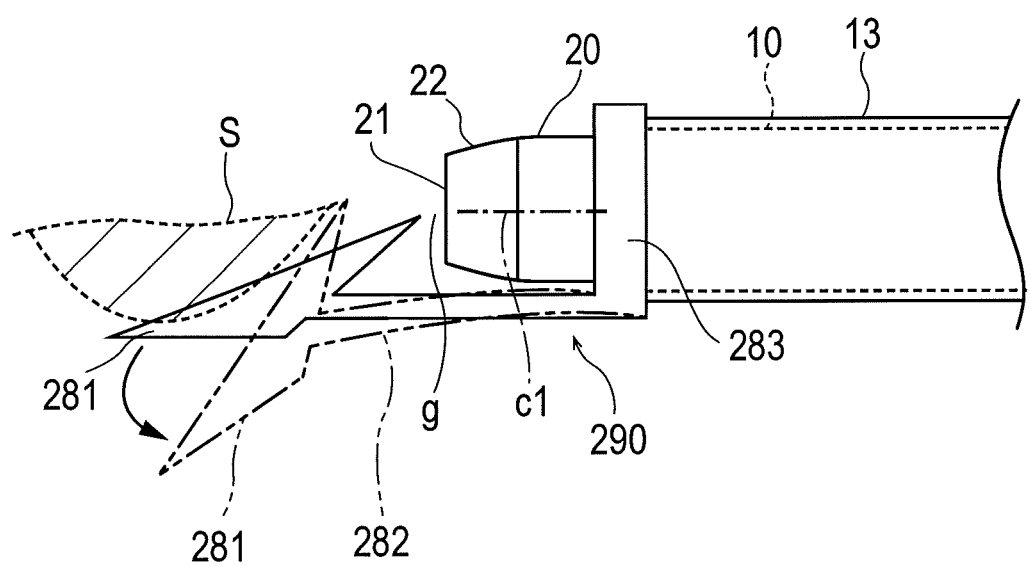
FIG. 14 is a lateral view depicting a distal member according to a modification 9 to the embodiment.

FIG. 14 is a lateral view depicting a distal member 290 according to a modification 9.

The distal member 290 according to the present modification has a substantially same shape as that of the distal member 280 according to the modification 8 described hereinabove. However, the distal member 290 is different from the distal member 280 in that the guide portion 281 and the supporting portion 282 of the distal member 280 are configured for deformation such that they are spaced apart from the rotating member 20 through contact thereof with the stenosis S.

A manner when the distal member 290 is deformed is indicated by a two-dot chain line in FIG. 14. Since the guide portion 281 and the supporting portion 282 are configured for deformation when the distal member 290 contacts with the stenosis S, when the stenosis S is to be cut, the distal member 290 can prevent excessive pressing force from being applied to the stenosis S, and this makes it possible to perform a treatment with appropriate cutting force. Further, in such a case that the cutting portion 22 is brought into contact with a normal tissue or in a like case, the distal member 290 can prevent the normal tissue from being damaged. Note that, as an alternative, only one of the guide portion 281 and the supporting portion 282 may be formed for deformation while the other member is configured as a member having a comparatively high rigidity such that no deformation is caused by contact with the stenosis S.

Figure 15A:
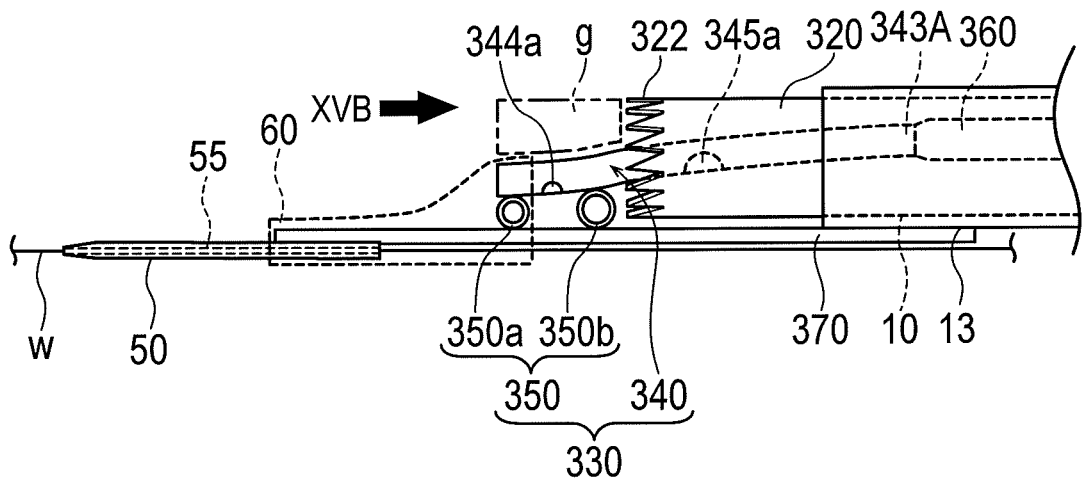
FIG. 15A is a lateral view depicting a distal member according to a modification 10 to the embodiment.
Figure 15B:
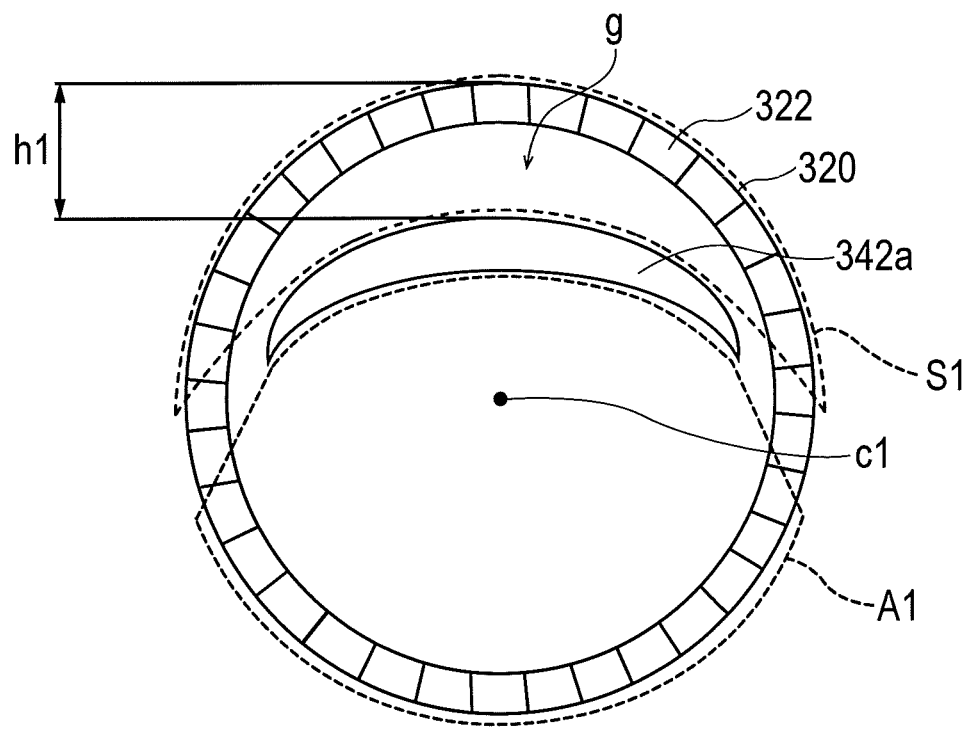
FIG. 15B is a view briefly illustrating a positional relationship between a guide portion and a rotating member as viewed from a direction indicated by an arrow mark XVB of FIG. 15A.

FIG. 15A is a lateral view depicting a distal member 330 according to a modification 10, and FIG. 15B is a view briefly illustrating a positional relationship between a guide portion 340 and a rotating member 320 as viewed from a direction indicated by an arrow mark XVB of FIG. 15A. Further, FIGS. 16A and 16B are a perspective view and a plan view depicting the guide portion 340 according to the modification 10, respectively.

As depicted in FIG. 15A, the distal member 330 according to the present modification has the guide portion 340, and a supporting portion 350 which supports the guide portion 340 in the heightwise direction. The supporting portion 350 forms, on the distal end side of the rotating member 320, a space g which spaces the guide portion 340 and the rotating member 320 from each other.

Figure 16A:
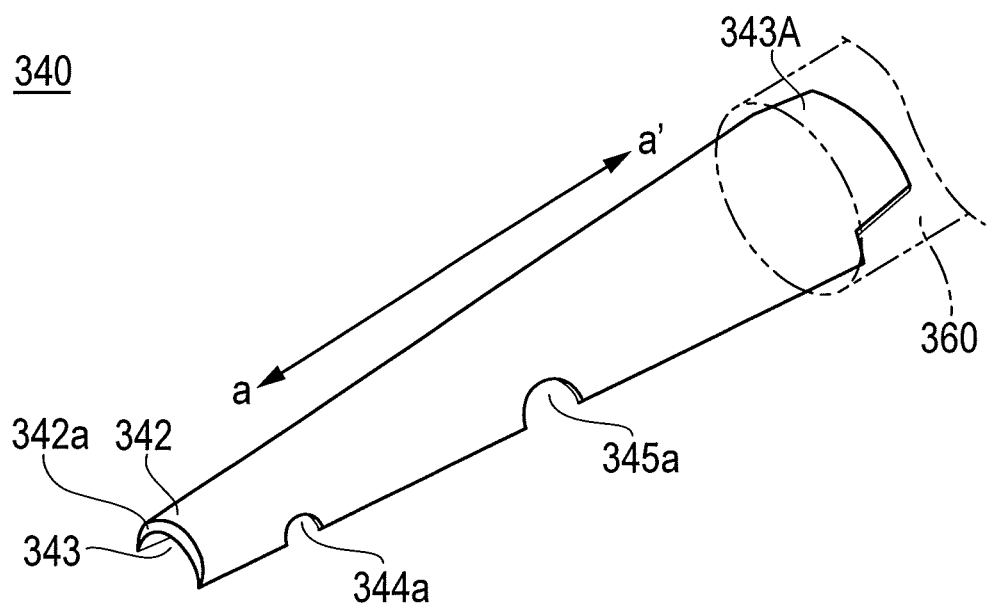
FIG. 16A is a perspective view depicting a guide portion according to the modification 10 to the embodiment.
Figure 16B:
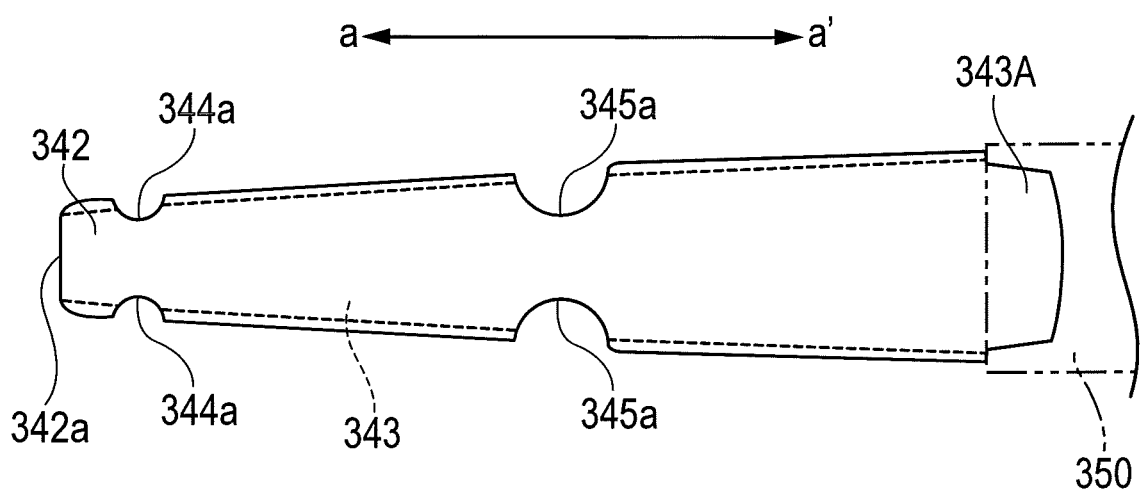
FIG. 16B is a plan view depicting the guide portion according to the modification 10 to the embodiment.

As depicted in FIGS. 16A and 16B, the guide portion 340 is configured from a plate-like member extending in an axial direction (direction of an arrow mark a-a' in FIGS. 16A and 16B).

The guide portion 340 is formed in a shape curved to one face side (in the example depicted, to the upper face side). Further, the guide portion 340 is formed in such a shape that the width thereof increases from a distal end portion 342 of the guide portion 340 toward the proximal end side (shape in which the widthwise dimension in the upward and downward direction in FIG. 16B increases from the distal end portion 342 side toward the proximal end side).

As depicted in FIGS. 16A and 16B, a distal end face 342a of the guide portion 340 is formed in a shape curved like a crescent shape as viewed from the front face side (in a tapering shape such that a center portion has the greatest area and the area decreases toward the opposite end sides as viewed in front elevation). Note that the sectional shapes at different portions of the guide portion 340 in the axial direction (sectional shapes in a direction perpendicular to the axial direction) are formed in shapes curved like a crescent shape similarly to the distal end face 342a.

A space portion 343 is formed on the inner face side of the guide portion 340. The inner face of the guide portion 340 is formed in a shape curved corresponding to an outer shape of the guide portion 340.

The guide portion 340 has a plurality of opening portions 344a formed therein in a communicating relationship with the space portion 343. The opening portions 344a allow, when a treatment for the stenosis S is performed, debris D and so forth to flow into the guide portion 340 similarly to the side face opening portion 36b (refer to FIG. 5B) described hereinabove.

A predetermined supporting member 360 is connected to a proximal end portion 343A of the guide portion 340. The proximal end portion 343A of the guide portion 340 can be formed, for example, in a partly cut shape as depicted in FIGS. 16A and 16B.

As depicted in FIG. 15A, the supporting portion 350 has a first supporting portion 350a and a second supporting portion 350b. The first supporting portion 350a is disposed on the distal end side with respect to the second supporting portion 350b.

The first supporting portion 350a and the second supporting portion 350b are each formed from a cylindrical shape member extending in a direction crossing with the axial direction (in the depthwise direction with respect to the plane of FIG. 15B). Further, the first supporting portion 350a has an outer diameter smaller than that of the second supporting portion 350b. The guide portion 340 is fixed to the supporting portions 350a and 350b. The guide portion 340 is disposed in a shape in which it is curved toward the distal end side corresponding to an outer diameter difference between the supporting portions 350a and 350b.

In accordance with an exemplary embodiment, a bar-like member 370 is fixed to an outer surface of the cover member 13 such that it extends in the axial direction. The guide wire insertion portion 50 is disposed at a distal end portion of the bar-like member 370 and has the guide wire lumen 55 formed therein.

The supporting member 360 connected to the guide portion 340 is inserted in the inside of the elongate member 10. The supporting member 360 can help prevent the guide portion 340 from dropping off from the elongate member 10 or the like.

A distal end portion of the guide portion 340, the guide wire insertion portion 50 and the bar-like member 370 are connected to each other through a covering member (for example, a known heat shrinkable tube) 60.

The rotating member 320 has a cutting portion 322 formed from a blade (for example, a serrated blade) projecting unevenly on the distal end side of the rotating member 320. Note that also it is possible to form the cutting portion 322, for example, in a trephine shape (refer to FIG. 3A) indicated in connection with the embodiment described hereinabove.

Operation of the present modification is described with reference to FIG. 15B.

As depicted in FIG. 15B, a guide face A1 (region in which the cutting portion 322 of the rotating member 320 is partly covered with the guide portion 340 and the supporting portion 350) is formed on one side of the guide portion 340 with respect to the distal end face 342a (in the example depicted in FIG. 15B, on the lower side). Consequently, the range over which the cutting portion 322 of the rotating member 320 and a blood vessel wall or the like can contact with each other (height h1 of the effective cutting range) is limited to a predetermined size. Therefore, similarly as in the embodiment described hereinabove, the risk that the cutting portion 322 may penetrate a blood vessel wall can be reduced significantly.

Further, in the present modification, since the guide portion 340 is configured from a plate-like member, the guide face A1 of a comparatively large area can be formed readily on the lower side of the guide portion 340. Further, even if such a situation occurs that, while a treatment for the stenosis S is being performed, the guide portion 340 tends to be inadvertently displaced upwardly or downwardly in FIG. 15B, since end portions of the guide portion 340 in the widthwise direction (opposite left and right end portions in FIG. 15B) contact with and are supported by the inner circumferential face of the rotating member 320, the positional displacement of the guide portion 340 can be suppressed.

Further, since the sectional shape taken in a direction orthogonal to the axial direction of the guide portion 340 is formed in a shape curved like a crescent shape, the stenosis S can be cut away in a crescent shape of a comparatively small thickness. Therefore, cut chips (debris D) of the stenosis S can be prevented from causing clogging in the inside of the elongate member 10.

Note that, as the constituent materials of the members described in connection with the modification 10 (rotating member 320, guide portion 340, supporting portion 350 and so froth), for example, resin materials and metal materials exemplified in the description of the embodiment and the other modifications described hereinabove can be used. Further, as the connection methods for the members, known methods (welding, adhesion and so forth) can be adopted.

Note that the particular shapes of the guide portion 340 and the supporting portion 350 are not limited to those depicted in FIGS. 15A to 16B and can be changed. For example, also it is possible to configure the guide portion 340 from a member in the form of a flat plate having a rectangular cross section or from a plate-like member or the like having cross sectional shapes different at different portions in the axial direction. Also where the cross sectional shape of the guide portion 340 is configured from a curved shape, it may be a shape different from a crescent shape, and also it is possible to change the curvature and so forth of the curved shape. Furthermore, while the example is described above in which the two supporting portions 350a and 350b are used as the supporting portion 350, the supporting portion 350 may otherwise be configured from a single member or configured from three or more members.

Although the modifications to the distal member are described above, the shape, structure and so forth of the distal member are not restricted particularly only if the distal member has at least one guide portion disposed on the distal end side of a rotating member with a space interposed therebetween and a supporting portion for supporting the guide portion thereon and are not restricted to the configurations of the distal member described hereinabove in connection with the embodiment and the modifications.

While the medical device according to the present disclosure has been described in connection with the embodiment thereof, the present disclosure is not limited only to the contents described in connection with the embodiment but can be altered based on the description of the claims.

For example, the living body lumen which becomes a target of application of the medical device and the treatment method is not limited to a blood vessel, but may be, for example, a vascular, a ureter, a bile duct, a uterine tube, a hepatic duct or the like. Further, the object which becomes a target of cutting is not limited to a stenosis or a blocking portion. Further, while, in the description of the embodiment, a treatment for cutting a stenosis formed at part in a circumferential direction of a wall portion of a living body lumen is exemplified, the application of the medical device is not limited by the shape, the position in a circumferential direction and so forth of the stenosis.

The structure of the portions, the displacement of the members and so forth of the medical device described hereinabove in connection with the embodiment can be changed, and omission of use of an additional member described with reference to the drawings, use of other additional members and so forth can be performed. Further, the configurations of the distal members described hereinabove in connection with the embodiment and the modifications can be combined unless the functions of them are damaged.

The detailed description above describes a medical device for cutting an object existing in a living body lumen. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting an object in a living body lumen, the medical device comprising:
   a rotatable elongate member;
   a rotating member having a cutting portion cutting the object and disposed on a distal end side of the elongate member and configured to rotate together with rotation of the elongate member;
   a distal member having a guide portion disposed on a distal end side of the rotating member and spaced apart from the rotating member and a supporting portion which supports the guide portion and defines a dimension of a space in an axial direction of the elongate member;
   the guide portion or the supporting portion being disposed at a position at which the guide portion or the supporting portion overlaps with part of the cutting portion and exposes part of the cutting portion as viewed from the distal end side of the distal member;
   wherein, in a state in which no external force is applied, the supporting portion disposes a center position in a heightwise direction, which crosses with the axial direction, of the guide portion at a position displaced in the heightwise direction from the center position of the rotating member;
   the guide portion or the supporting portion being disposed so as to overlap with the center position of the rotating member and part of a circumferential edge of the rotating member as viewed from the distal end side of the distal member; and
   wherein the guide portion and the rotating member have shapes different from each other as viewed from the distal end side of the distal member, and the guide portion has an outer circumferential length shorter than an outer circumferential length of the rotating member.

2. The medical device according to claim 1,
   wherein the rotating member has a hollow shape having a lumen, and
   at least part of the object cut by the cutting portion is collected into the lumen of the rotating member through the space.

3. The medical device according to claim 1,
   wherein the guide portion is disposed opposite to the supporting portion with respect to the center position of the rotating member.

4. The medical device according to claim 1, further comprising
   a cover member configured to cover at least part of the elongate member and disposed against interlocking rotation with rotation of the rotating member, and wherein the distal member is connected to the cover member so as not to rotate in an interlocking relationship with rotation of the rotating member.

5. The medical device according to claim 1,
wherein the guide portion and/or the supporting portion is configured for deformation so as to be spaced apart from the rotating member through contact of the rotating member with the object.

6. The medical device according to claim 1,
wherein the guide portion and the supporting portion of the distal member are configured integrally.

7. The medical device according to claim 1,
wherein the guide portion is configured from a member in the form of a plate extending in the axial direction.

8. The medical device according to claim 7,
wherein the guide portion is shaped such that a cross section taken along a direction orthogonal to the axial direction is curved in a crescent shape.

9. The medical device according to claim 1,
wherein the guide portion and/or the supporting portion is configured for deformation so as to be spaced apart from the rotating member through contact of the rotating member with the object.

10. A medical device for cutting an object in a living body lumen, the medical device comprising:
a rotatable elongate member;
a rotating member having a cutting portion cutting the object and disposed on a distal end side of the elongate member and configured to rotate together with rotation of the elongate member;
a distal member disposed on a distal end side of the cutting portion and overlaps with part of the cutting portion and exposes part of the cutting portion as viewed from the distal end side of the distal member; and
wherein a ratio of a region in which the distal member and the cutting portion overlap with each other in a circumferential direction as viewed from the distal end side of the distal member is lower than a ratio of another region in which the cutting portion is exposed from the distal member in a circumferential direction.

11. The medical device according to claim 10, further comprising
a cover member configured to cover at least part of the elongate member and disposed against interlocking rotation with rotation of the rotating member, and
wherein the distal member is connected to the cover member so as not to rotate in an interlocking relationship with rotation of the rotating member.

12. A medical device for cutting an object in a living body lumen, the medical device comprising:
a rotatable elongate member;
a rotating member having a cutting portion cutting the object and disposed on a distal end side of the elongate member and configured to rotate together with rotation of the elongate member;
a distal member having a guide portion disposed on the distal end side of the rotating member and spaced apart from the rotating member and a supporting portion which supports the guide portion and defines a dimension of a space in an axial direction of the elongate member;
the guide portion or the supporting portion being disposed at a position at which the guide portion or the supporting portion overlaps with part of the cutting portion and exposes part of the cutting portion as viewed from the distal end side of the distal member; and wherein the supporting portion has an outer circumferential length shorter than an outer circumferential length of the rotating member.

13. The medical device according to claim 12, further comprising
a cover member configured to cover at least part of the elongate member and disposed against interlocking rotation with rotation of the rotating member, and
wherein the distal member is connected to the cover member so as not to rotate in an interlocking relationship with rotation of the rotating member.

14. The medical device according to claim 10,
wherein the guide portion and/or a supporting portion is configured for deformation so as to be spaced apart from the rotating member through contact of the rotating member with the object.

15. A medical device for cutting an object in a living body lumen, the medical device comprising:
a rotatable elongate member that is rotatable along a rotation axis;
a cutting portion disposed on a distal end side of the rotatable elongate member and configured to rotate together with rotation of the elongate member;
a guide portion extending from an inside of the cutting portion to a distal side of the cutting portion;
a portion of a cross section of the guide portion is formed in a generally rectangular shape, a flat plate, a crescent shape, an elliptical shape, or a tapering shape, where the cross section is taken at the distal end side of the cutting portion along a direction perpendicular to the rotational axis of the rotatable elongate member; and
a supporting portion which supports the guide portion, and wherein the supporting portion is configured to be connected to a cover member that covers the rotatable elongate member.

16. The medical device according to claim 15, wherein a center position of the guide portion at the cross section is different from a center position of the cutting portion at the cross section.

17. The medical device according to claim 15, wherein the guide portion is fixed to the supporting portion, to the rotatable member being rotatable relative to the guide portion, and wherein the guide portion does not rotate.

18. The medical device according to claim 15, further comprising:
a supporting portion which supports the guide portion, and wherein the guide portion has a side facing the support portion, and the side of the guide portion is formed in the flat or concave shape.

19. The medical device according to claim 17, wherein a distance between the distal end side of the cutting portion and a distal end side of the guide portion is fixed.

20. The medical device according to claim 15, wherein a position of the guide portion relative to the cutting portion is configured such that a distance between an outer surface of the cutting portion at a topmost section of the cutting portion and a topmost section of the guide portion is less than a thickness of a blood vessel wall of the living body lumen.

21. The medical device according to claim 15, wherein extension of the guide portion from the inside of the cutting portion inclines relative to the rotational axis of the rotatable elongate member.

22. The medical device according to claim 15, wherein the tapering shape of the portion of the cross section of the guide portion includes a center portion having a greatest area and areas decreasing toward opposite end sides as viewed in front elevation.

23. The medical device according to claim 15, wherein the flat plate has a generally rectangular shape or is a plate-like member having cross sectional shapes different at different portions in an axial direction.

24. A medical device for cutting an object in a living body lumen, the medical device comprising:
   a rotatable elongate member that is rotatable along a rotation axis;
   a cutting portion disposed on a distal end side of the rotatable elongate member and configured to rotate together with rotation of the elongate member;
   a guide portion extending from an inside of the cutting portion to a distal side of the cutting portion;
   a portion of a cross section of the guide portion is formed in a generally rectangular shape, a flat plate, a crescent shape, an elliptical shape, or a tapering shape, where the cross section is taken at the distal end side of the cutting portion along a direction perpendicular to the rotational axis of the rotatable elongate member; and
   a supporting portion which supports the guide portion, and wherein the guide portion or the supporting portion is disposed at a position at which the guide portion overlaps with part of the cutting portion and exposes part of the cutting portion as viewed from a distal end side of the medical device.

25. A medical device for cutting an object in a living body lumen, the medical device comprising:
   a rotatable elongate member that is rotatable along a rotation axis;
   a cutting portion disposed on a distal end side of the rotatable elongate member and configured to rotate together with rotation of the elongate member;
   a guide portion extending from an inside of the cutting portion to a distal side of the cutting portion;
   a portion of a cross section of the guide portion is formed in a generally rectangular shape, a flat plate, a crescent shape, an elliptical shape, or a tapering shape, where the cross section is taken at the distal end side of the cutting portion along a direction perpendicular to the rotational axis of the rotatable elongate member;
   a supporting portion which supports the guide portion, and wherein the supporting portion is configured to connect the guide portion that extends from the inside of the cutting portion to a distal side of the cutting portion; and
   a guide wire insertion portion located outside of the cutting portion.

26. A medical device for cutting an object in a living body lumen, the medical device comprising:
   a rotatable elongate member that is rotatable along a rotation axis;
   a cutting portion disposed on a distal end side of the rotatable elongate member and configured to rotate together with rotation of the elongate member;
   a guide portion extending from an inside of the cutting portion to a distal side of the cutting portion;
   a portion of a cross section of the guide portion is formed in a generally rectangular shape, a flat plate, a crescent shape, an elliptical shape, or a tapering shape, where the cross section is taken at the distal end side of the cutting portion along a direction perpendicular to the rotational axis of the rotatable elongate member; and
   a supporting portion which supports the guide portion, and wherein the supporting portion is connected to the guide portion at a distal end of the guide portion and extends farther to a distal side of the medical device than the guide portion.

27. A medical device for cutting an object in a living body lumen, the medical device comprising:
   a rotatable elongate member that is rotatable along a rotation axis;
   a cutting portion disposed on a distal end side of the rotatable elongate member and configured to rotate together with rotation of the elongate member;
   a guide portion extending from an inside of the cutting portion to a distal side of the cutting portion;
   a portion of a cross section of the guide portion is formed in a generally rectangular shape, a flat plate, a crescent shape, an elliptical shape, or a tapering shape, where the cross section is taken at the distal end side of the cutting portion along a direction perpendicular to the rotational axis of the rotatable elongate member, wherein the tapering shape has a center portion having a greatest area and the area decreases toward opposite end sides.

28. A medical device for cutting an object in a living body lumen, the medical device comprising:
   a rotatable elongate member having a circumferential surface;
   a cover member that covers a circumferential surface of the rotatable elongate member;
   a cutting portion disposed on a distal end side of the rotatable elongate member and configured to rotate together with rotation of the elongate member;
   a guide portion extending from an inside of the cutting portion to a distal side of the cutting portion; and
   a supporting portion which supports the guide portion, the supporting portion including an elongate part that has a first end attached to a guide wire insertion portion and a second end fixedly attached to an outer circumference surface of the cover member.

29. The medical device according to claim 28, wherein the supporting portion is connected to the guide portion at a distal end of the guide portion and extends farther to a distal side of the medical device than the guide portion.

* * * * *